(12) United States Patent
Byun et al.

(10) Patent No.: US 8,227,093 B2
(45) Date of Patent: Jul. 24, 2012

(54) CYCLOMETALATED TRANSITION METAL COMPLEX AND ORGANIC ELECTROLUMINESCENCE DEVICE USING THE SAME

(75) Inventors: Young-Hun Byun, Yongin-si (KR); Hee-Kyung Kim, Anyang-si (KR); Lyong-Sun Pu, Seongnam-si (KR); Shinichiro Tamura, Seongnam-si (KR); Das Rupasree Ragini, Suwon-si (KR); Jong-Jin Park, Yongin-si (KR); Byoung-Ki Choi, Hwaseong-si (KR); Yi-Yeol Lyu, Yongin-si (KR); O-Hyun Kwon, Seoul (KR); Young-Mok Son, Hwaseong-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 1053 days.

(21) Appl. No.: 11/633,488

(22) Filed: Dec. 5, 2006

(65) Prior Publication Data
US 2007/0190358 A1 Aug. 16, 2007

(30) Foreign Application Priority Data

Feb. 11, 2006 (KR) .................. 10-2006-0013330
Aug. 18, 2006 (KR) .................. 10-2006-0078325

(51) Int. Cl.
*H01L 51/54* (2006.01)
*C09K 11/06* (2006.01)

(52) U.S. Cl. ........ 428/690; 428/917; 313/504; 313/506; 546/2; 546/6; 257/40; 257/E51.044; 252/301.16

(58) Field of Classification Search .................. 428/690, 428/917; 427/428.01; 435/7.4; 987/1, 17; 313/504, 506; 257/E51.049, E51.05; 549/43, 549/460; 585/26
See application file for complete search history.

(56) References Cited

U.S. PATENT DOCUMENTS

| | | | |
|---|---|---|---|
| 4,356,429 A | 10/1982 | Tang | |
| 2003/0072964 A1 * | 4/2003 | Kwong et al. | 428/690 |
| 2004/0053071 A1 * | 3/2004 | Igarashi et al. | 428/690 |

FOREIGN PATENT DOCUMENTS

JP 11-329734 11/1999

OTHER PUBLICATIONS

Thompson et al. "Mono- and di-nuclear ruthenium(II) complexes of the ambidentate ligand 3,3'-dihydroxy-2,2'-bipyridine: spectroscopic, electrochemical and mixed-valence properties." J. Chem. Soc., Dalton Trans., 1996, pp. 879-884.*
Cotton et al. "Advanced Inorganic Chemistry", John Wily and Sons, Inc. 6th Edition, pp. 101-1039, 1999.*
M. A. Baldo et al., "highly efficient phosphorescent emission from organic electroluminescent devices", Nature, vol. 395, Sep. 10, 1998, pp. 151-154.
Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tri(3-methylphenylphenyl-amino)triphenylamine (m-MTDATA), as Hole-Transport Materials", Adv. Mater. 1994, 6, No. 9, pp. 677-679.
S. Sprouse et al., "Photophysical Effects of Metal-Carbon σ Bonds in Ortho-Metalated Complexes of Ir(III) and Rh(III)", J. Am. Chem. Soc. 1984, 106, 6647-6653.
F. O. Garces et al., "Synthesis, Structure, Electrochemistry, and Photophysics of Methyl-Substituted Pheynylpyridine Ortho-Metalated Iridium(III) Complexes", Inorg. Chem. 1988, 27, 3464-3471.

* cited by examiner

*Primary Examiner* — Jennifer Chriss
*Assistant Examiner* — Michael H Wilson
(74) *Attorney, Agent, or Firm* — Robert E. Bushnell, Esq.

(57) ABSTRACT

Provided is a cyclometalated transition metal complex represented by Formula 1, Formula 2 or Formula 3:

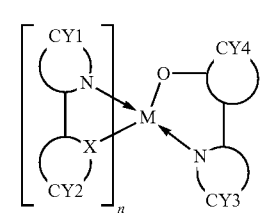

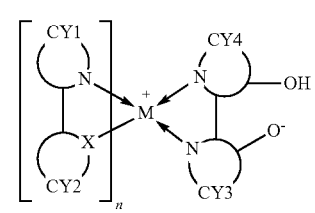

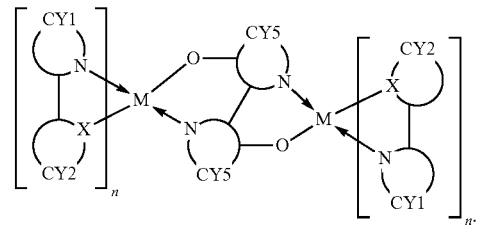

By including a new ancillary ligand, the cyclometalated transition metal complex can efficiently emit red light using a phosphor by intersystem crossing (ISC) of excitons to triplet states and then metal to ligand charge transfer (MLCT). An organic light emitting device prepared using the transition metal compound shows high luminous efficiency and high external quantum efficiency.

17 Claims, 5 Drawing Sheets

CYCLOMETALATED TRANSITION METAL COMPLEX AND ORGANIC ELECTROLUMINESCENCE DEVICE USING THE SAME

CROSS-REFERENCE TO RELATED PATENT APPLICATIONS AND CLAIM OF PRIORITY

This application claims the benefit of Korean Patent Application No. 10-2006-0013330, filed on Feb. 11, 2006, and 10-2006-0078325, filed on Aug. 18, 2006, in the Korean Intellectual Property Office, the disclosures of which are incorporated herein in their entirety by reference.

BACKGROUND OF THE INVENTION

1. Field of the Invention

The present invention relates to a cyclometalated transition metal complex and an organic light emitting device manufactured using the same, and more particularly, to a cyclometalated transition metal complex that can emit red light by triplet metal-to-ligand charge transfer (MLCT) and to an organic light emitting device manufactured to include an organic layer comprising the cyclometalated transition metal complex.

2. Description of the Related Art

Organic electroluminescent devices (organic EL devices) are self-emission display devices in which when a current is provided to a fluorescent or phosphor organic compound layer (hereinafter, referred to as organic layer), electrons and holes are combined together in the organic layer, thereby emitting light. Organic EL devices are lightweight, can be easily manufactured using few components, and have high image quality and wide viewing angles. In addition, they can realize a high degree of color purity and moving pictures, require low power consumption, and can operate at low voltages. Due to these advantages, they are suitable for use in portable electronics.

In a general structure of an organic EL device, an anode is formed on a substrate, and a hole transport layer, an emission layer, an electron transport layer, and a cathode are sequentially formed on the anode. The hole transport layer, the emission layer, and the electron transport layer are organic layers formed of organic compounds. An operational principle of an organic light emitting device having such a structure will now be described in detail. When a voltage is applied between the anode and the cathode, holes injected from the anode move to the emission layer through the hole transport layer, and electrons that are injected from the cathode move to the emission layer through the electron transport layer. In the emission layer, the electrons and holes recombine and thus excitons are generated and light having a wavelength corresponding to a band gap of a material is generated by radiative decay.

According to an emission mechanism, materials that are used to form an emission layer of an organic light emitting device are divided into fluorescent materials that use singlet excitons and phosphor materials that use triplet excitons. These fluorescent and phosphor materials themselves can be used to form an emission layer, or they can be doped on an appropriate host material to form an emission layer. As a result of electron excitation, singlet excitons and triplet excitons are formed in a host. At this time, a statistical generation ratio of singlet excitons to triplet excitons is 1:3.

When an organic light emitting device has an emission layer formed of a fluorescent material, triplet excitons that are generated in a host thereof are not used. On the other hand, when an organic light emitting device has an emission layer formed of a phosphor material, both singlet excitons and triplet excitons can be used such that internal quantum efficiency reaches 100% (Baldo, et al., Nature, Vol. 395, 151-154, 1998). Accordingly, an organic light emitting device that has an emission layer formed of a phosphor material shows much higher luminous efficiency than an organic light emitting device that has an emission layer formed of a fluorescent material.

When a heavy metal, such as Ir, Pt, Rh, or Pd, is introduced to an organic molecule, a triplet state and a singlet state are mixed together through spin-orbital coupling that occurs due to a heavy atom effect, thereby enabling transitions that is forbidden and effectively emitting a phosphor light even at room temperature.

Recently, a green light emitting material of which an internal quantum efficiency can reach 100% has been developed using a phosphor material.

Although transition metal complexes containing transition metals, such as Iridium or Platinum, are being developed as a highly efficient emission materials using phosphor materials, their luminous efficiencies are not suitable for highly efficient full-color displays or white light emission applications having low power consumption.

Red light emission for full-color displays can be realized if a luminous efficiency of about 3 lm/W is realized, but currently, the maximum luminous efficiency only reaches as low as 1 lm/W.

Accordingly, there is a need to develop a red light emitting material having improved light emission properties by overcoming such conventional technical limitations in the development of red light emitting materials.

SUMMARY OF THE INVENTION

The present invention provides a cyclometalated transition metal complex that efficiently emits red light by triplet metal-to-ligand charge transfer (MLCT).

The present invention also provides an organic light emitting device that efficiently emits red light.

According to an aspect of the present invention, there is provided a cyclometalated transition metal complex represented by formula 1 or formula 2:

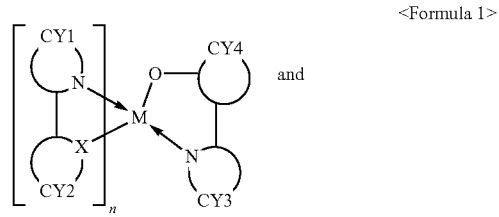
<Formula 1>

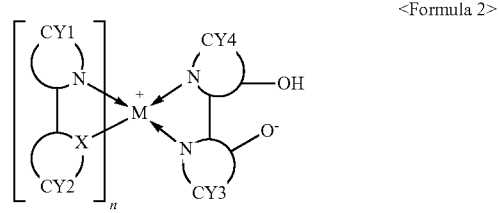
<Formula 2> where M is a transition metal;

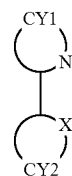

is a mono anionic bidentate chelating ligand (hereinafter "first mono anionic bidentate chelating ligand");

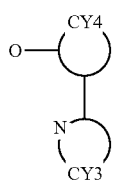

is a mono anionic bidentate chelating ligand (hereinafter "second mono anionic bidentate chelating ligand");

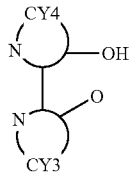

is a mono anionic bidentate chelating ligand (hereinafter "third mono anionic bidentate chelating ligand");
X is C, S, O, or N;
CY1, CY2, CY3, and CY4 are each independently an aromatic ring or an aliphatic ring; and
n is 1 or 2.

According to another aspect of the present invention, there is provided a cyclometalated transition metal complex represented by Formula 3:

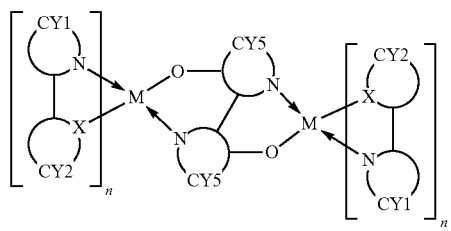

Formula 3 where M is a transition metal;

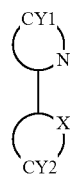

is a first mono anionic bidentate chelating ligand;

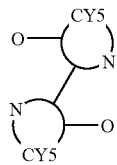

is a di-anionic tetradentate chelating ligand;
X is C, S, O, or N;
CY1, CY2, and CY5 are aromatic or aliphatic rings; and
n is 1 or 2.

In the cyclometalated transition metal complex, the first mono anionic bidentate chelating ligand may be selected from ligands represented by formulae below:

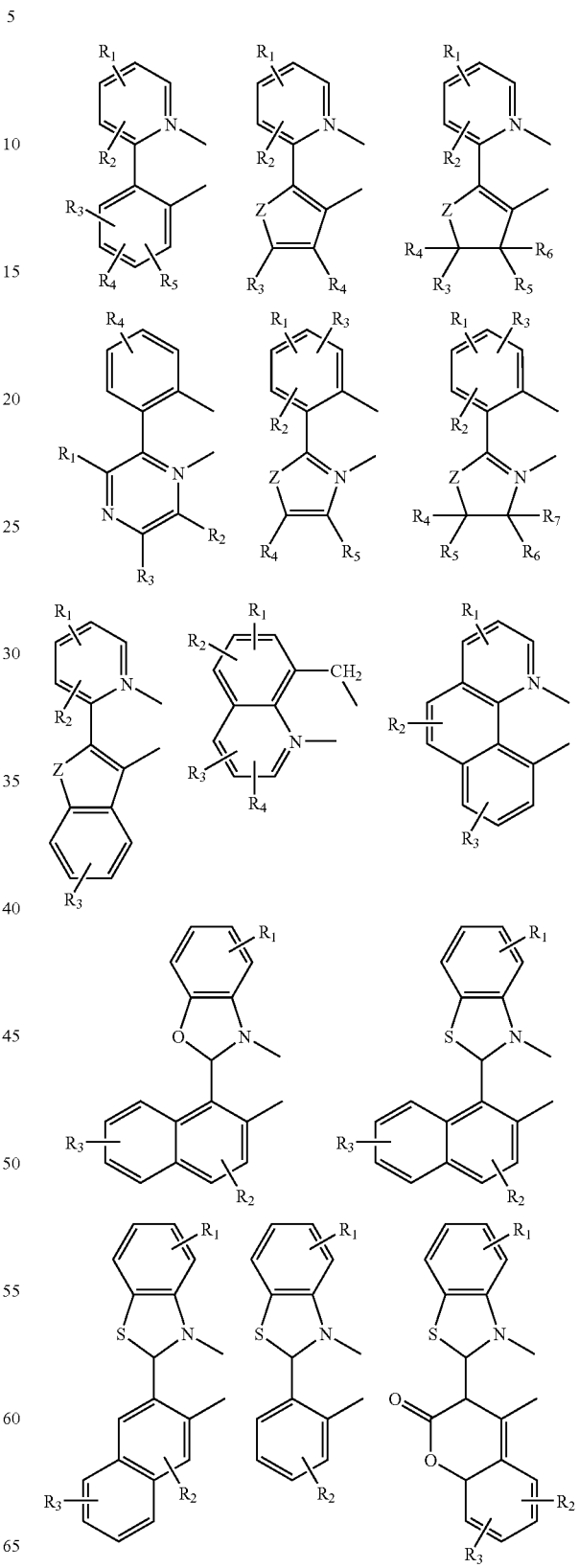

-continued

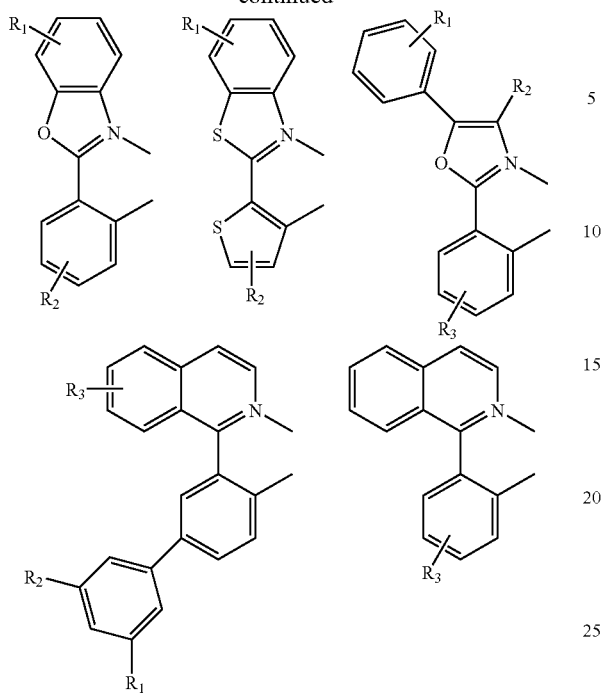

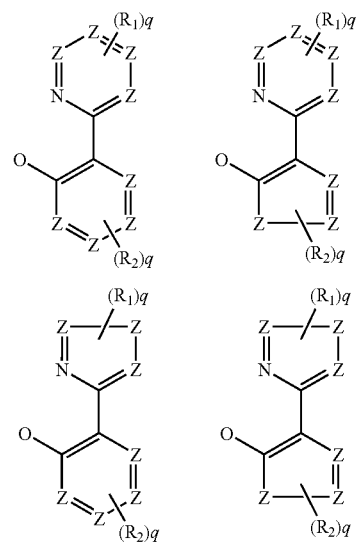

where Z is S, O, or NR$_8$; and

R$_1$, R$_2$, R$_3$, R$_4$, R$_5$, R$_6$, R$_7$, and R$_8$ are each independently hydrogen, halogen, OH, CF$_3$, CN, silyl, alkyl, aryl, alkoxy, aryloxy, amino, or arylene, wherein adjacent Rs may be fused together to form a five- to seven-membered aliphatic or aromatic ring.

In the cyclometalated transition metal complex, the second mono anionic bidentate chelating ligand may be selected from ligands represented by formulae below:

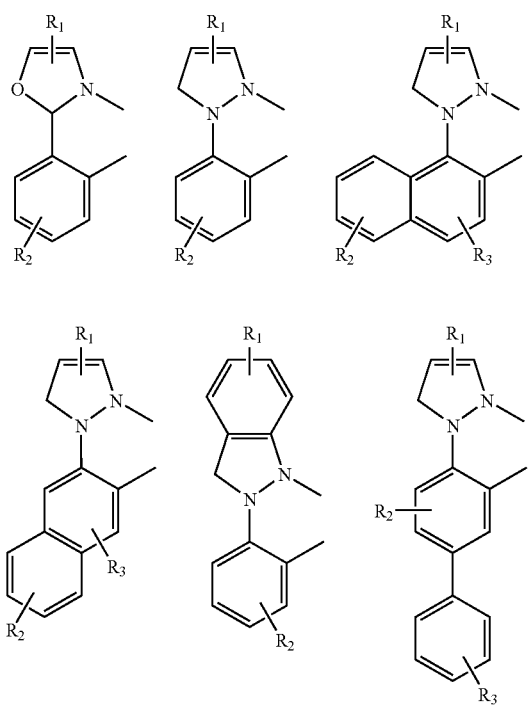

where Z is C, N, O, S, or P;

q is an integer from 0 to 5; and

R$_1$ and R$_2$ are each independently hydrogen, halogen, OH, CF$_3$, CN, silyl, alkyl, aryl, alkoxy, aryloxy, amino, or arylene, wherein adjacent Rs may be fused together to form a five- to seven-membered aliphatic or aromatic ring.

In the cyclometalated transition metal complex, the second mono anionic bidentate chelating ligand may be selected from ligands represented by formulae below:

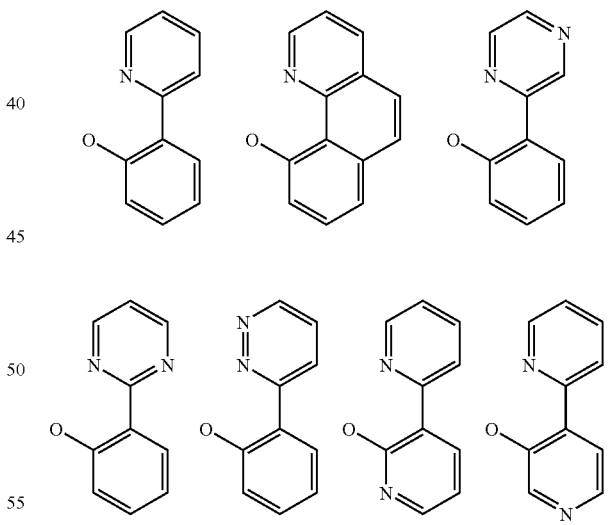

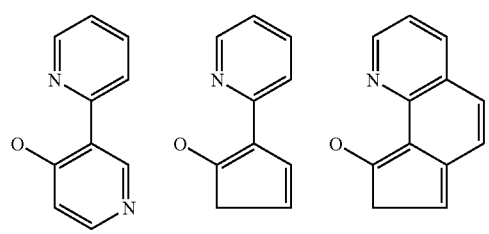

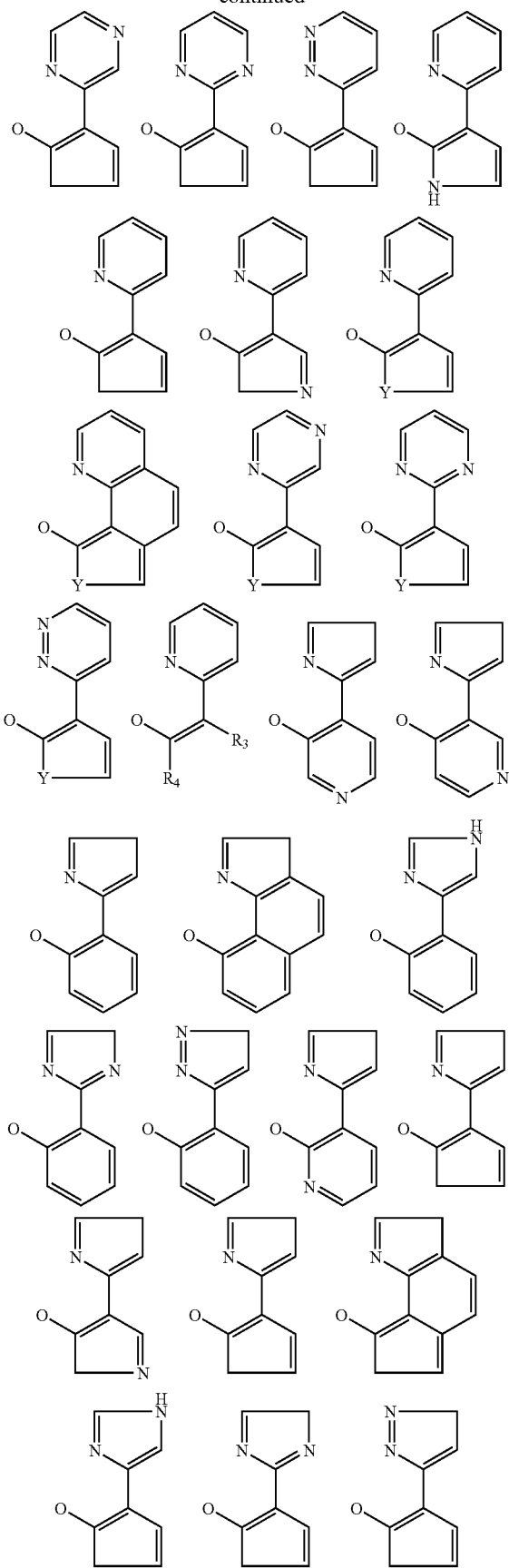

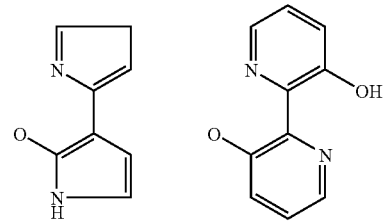

In the cyclometalated transition metal complex, the third mono anionic bidentate chelating ligand may be selected from ligands represented by formulae below:

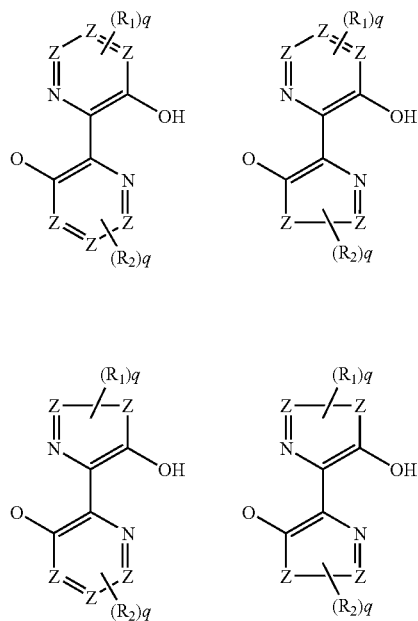

where Z is C, N, O, S, or P;

q is an integer from 0 to 5; and $R_1$ and $R_2$ are each independently hydrogen, halogen, OH, $CF_3$, CN, silyl, alkyl, aryl, alkoxy, aryloxy, amino, or arylene, wherein adjacent Rs may be fused together to form a five- to seven-membered aliphatic or aromatic ring.

In the cyclometalated transition metal complex, the di-mono-bidentate chelating ligand may be selected from ligands represented by formulae below:

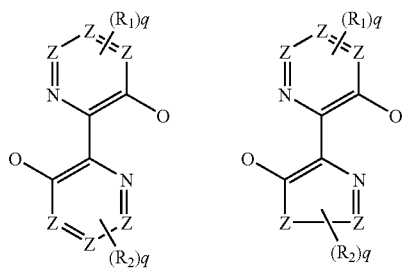

-continued

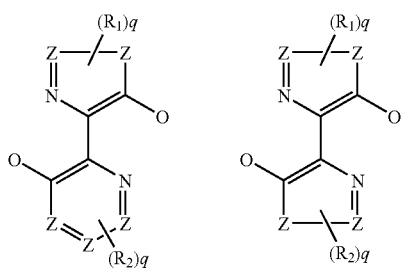

where Z is C, N, O, S, or P;

q is an integer from 0 to 5; and $R_1$ and $R_2$ are each independently hydrogen, halogen, OH, $CF_3$, CN, silyl, alkyl, aryl, alkoxy, aryloxy, amino, or arylene, wherein adjacent Rs may be fused together to form a five- to seven-membered aliphatic or aromatic ring.

In the cyclometalated transition metal complex, the di-mono-bidentate chelating ligand can be selected from ligands represented by formulae below:

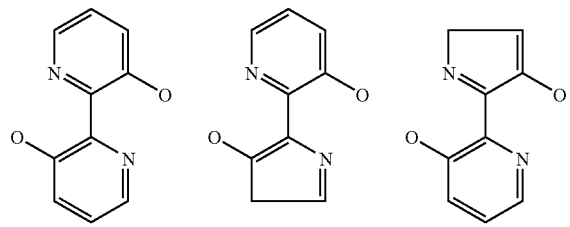

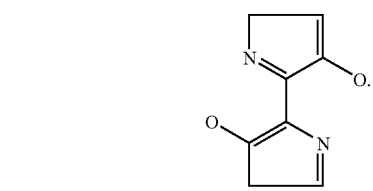

In the cyclometalated transition metal complex, the M can be Ru, Rh, Os, Ir, Pt, or Au.

In the cyclometalated transition metal complex, the M can be Ir.

In the cyclometalated transition metal complex, the transition compound of Formula 1 or Formula 2 is a complex represented by one of formulae below:

<Formula 4>

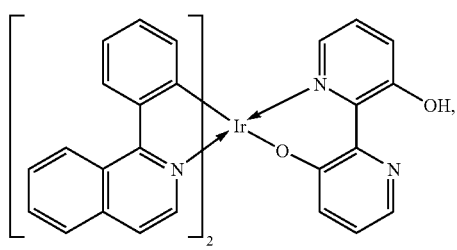

<Formula 5>

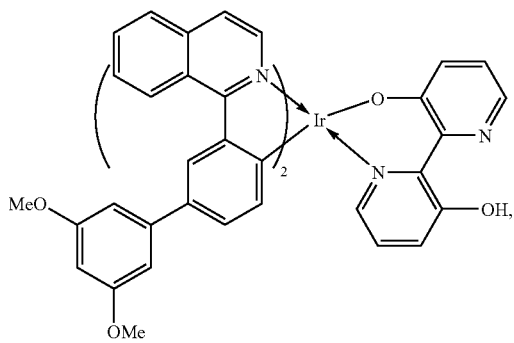

<Formula 6>

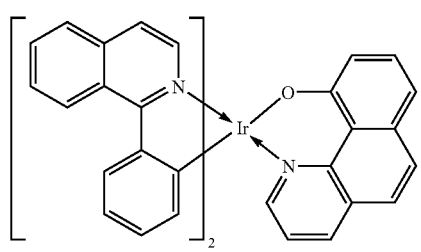

<Formula 7>

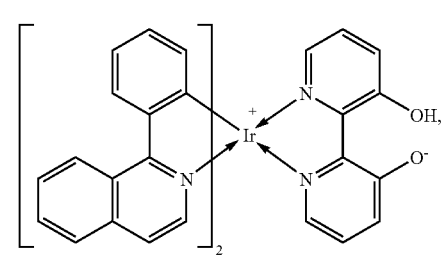

<Formula 8>

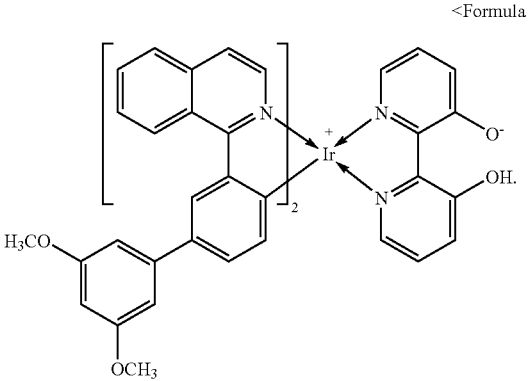

In the cyclometalated transition metal complex, the transition compound of Formula 3 can be a complex represented by one of formulae below:

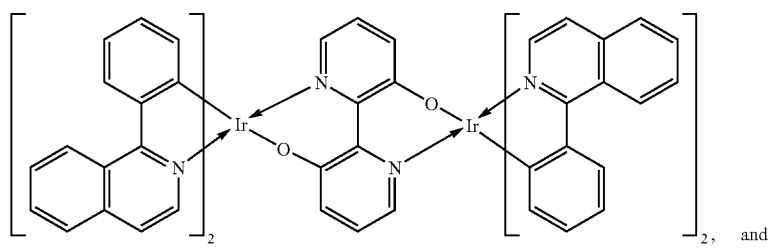

Formula 9

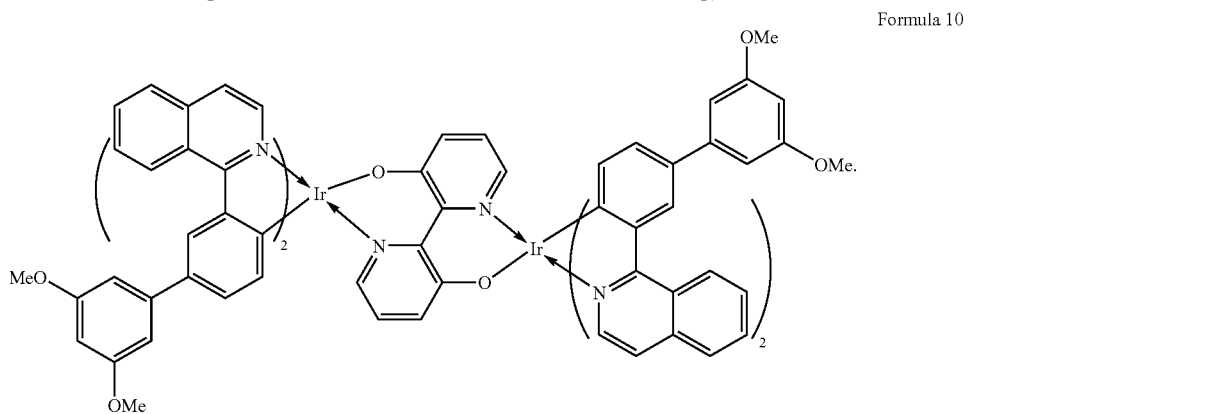

, and

Formula 10

According to another aspect of the present invention, there is provided an organic light emitting device including an organic layer interposed between a pair of electrodes, the organic layer containing the cyclometalated transition metal complex.

The organic layer may further contain at least one material selected from the group consisting of one or more kinds of polymer hosts, a mixture of a polymer host and a low molecular host, a low molecular host, and a non-luminous polymer matrix.

The organic layer may further contain a green emission material or a blue emission material.

A cyclometalated transition metal complex according to the present invention includes a new ancillary ligand, thereby efficiently emit a red phosphor light through intersystem crossing (ISC) to triplets and then metal to ligand charge transfer (MLCT). An organic light emitting device manufactured using the transition metal complex shows higher luminous efficiency and higher external quantum efficiency than a conventional organic light emitting device in a red wavelength region.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
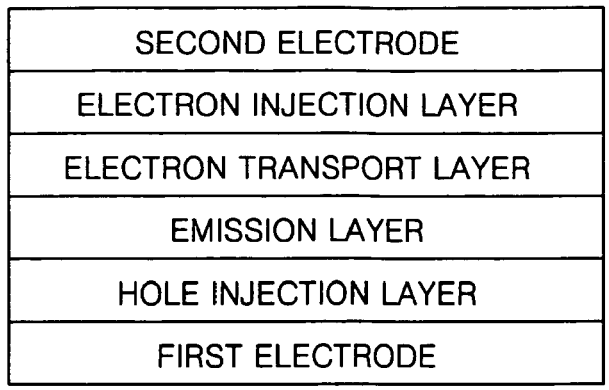
FIGS. 1A through 1C are sectional views of organic light emitting devices according to embodiments of the present invention.

The present invention will now be described more fully with reference to the accompanying drawings, in which exemplary embodiments of the invention are shown.

A cyclometalated transition metal complex according to an embodiment of the present invention can be represented by Formula 1 or Formula 2:

<Formula 1>

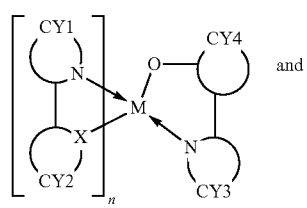

and

<Formula 2>

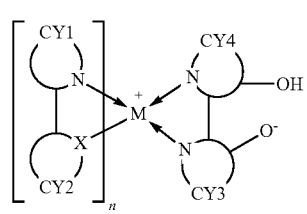

where M is a transition metal;

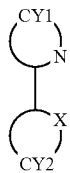

is a first mono anionic bidentate chelating ligand;

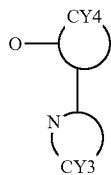

is a second mono anionic bidentate chelating ligand;

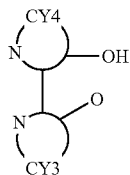

is a third mono anionic bidentate chelating ligand;

X is C, S, O, or N;

CY1, CY2, CY3, and CY4 are aromatic or aliphatic rings; and n is 1 or 2.

The complex of Formula 1 can be an isomer of the complex of Formula 2 and vice versa, according to the kind of a ligand.

A cyclometalated transition metal complex according to another embodiment of the present invention can be a binuclear complex represented by Formula 3:

<Formula 3>

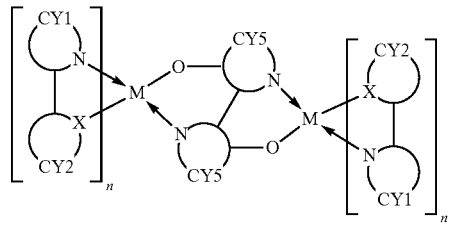

where M is a transition metal;

is a first mono anionic bidentate chelating ligand;

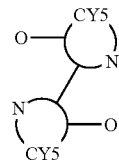

is a di-anionic tetradentate chelating ligand;

X is C, S, O, or N;

CY1, CY2, and CY5 are aromatic or aliphatic rings; and n is 1 or 2.

The cyclometalated transition metal complexes of Formulae 1 through 3 are transition metal complexes in which the first monoanionic bidentate chelating ligand acting as a primary ligand, and the second monoanionic bidentate chelating ligand, the third monoanionic bidentate chelating ligand, or di-anionic tetradentate chelating ligand acting as an ancillary ligand are coordinated. The cyclometalated transition metal complexes of Formulae 1 through 3 are characterized in that a new ancillary ligand is coordinated therein. Since the new ancillary ligand is coordinated in the cyclometalated transition metal complex, an organic light emitting device manufactured using such cyclometalated transition metal complexes shows higher luminous efficiency than organic light emitting devices manufactured using a conventional red fluorescent material or red phosphor material.

In Formulae 1 through 3, CY1, CY2, CY3, CY4 and CY5 are aromatic or aliphatic rings which may include heteroaromatic or heteroaliphatic rings which include at least one hetero atom and which may include aromatic or aliphatic rings substituted with at least one substituent.

The substituent may be OH, $CF_3$, CN, silyl, alkyl, aryl, alkoxy, aryloxy, amino, or arylene, wherein adjacent substituents may further be fused together to form a five to seven membered aliphatic or aromatic ring.

In the substituent, the alkyl group may have 1 to 30 carbon atoms, the aryl group may have 5 to 30 carbon atoms, the alkoxy group may have 1 to 30 carbon atoms, the aryloxy group may have 5 to 30 carbon atoms, and the arylene group may have 2 to 30 carbon atoms.

In the cyclometalated transition metal complexes of Formulae 1 through 3, the first mono anionic bidentate chelating ligand can be preferably selected from ligands represented by formulae below:

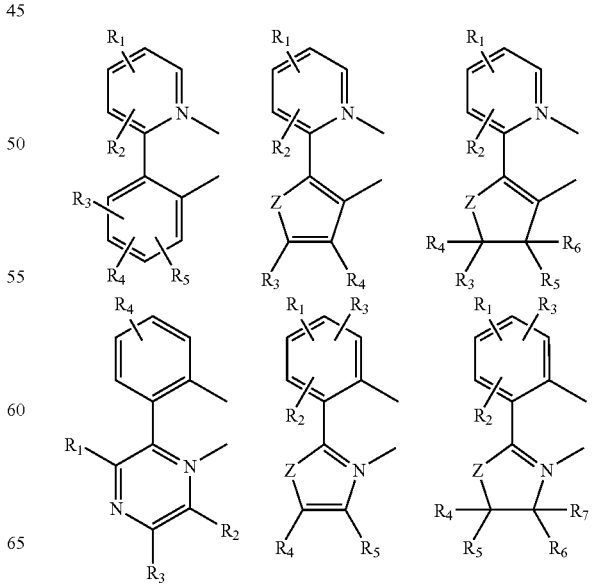

-continued

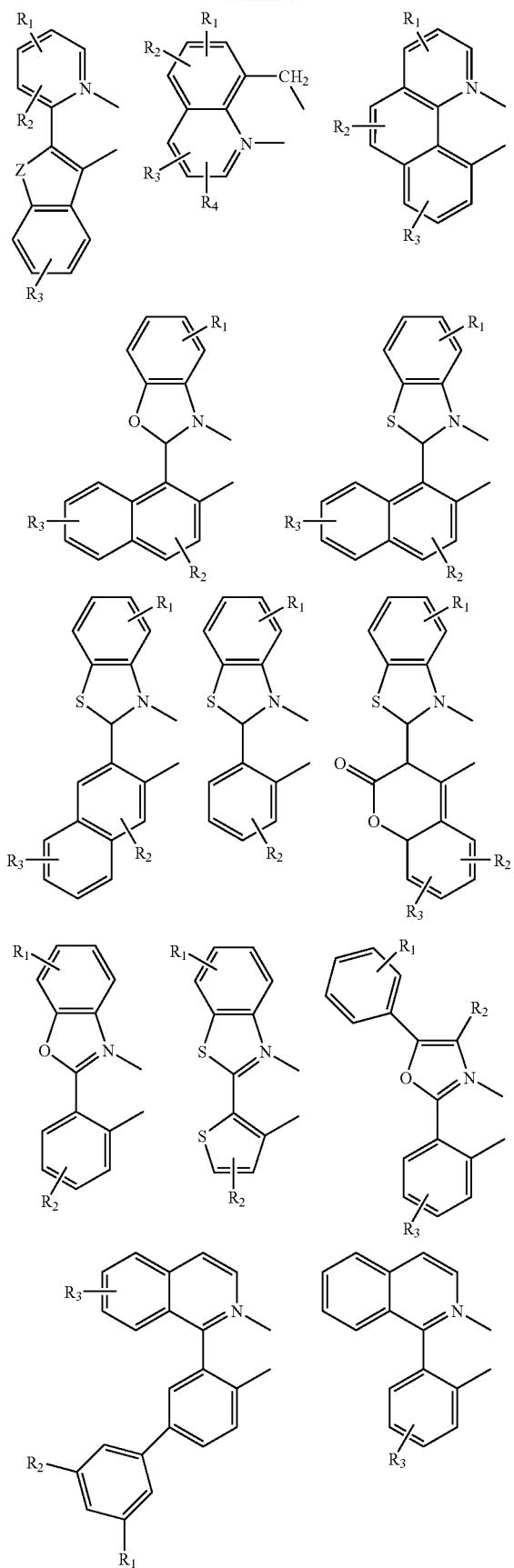

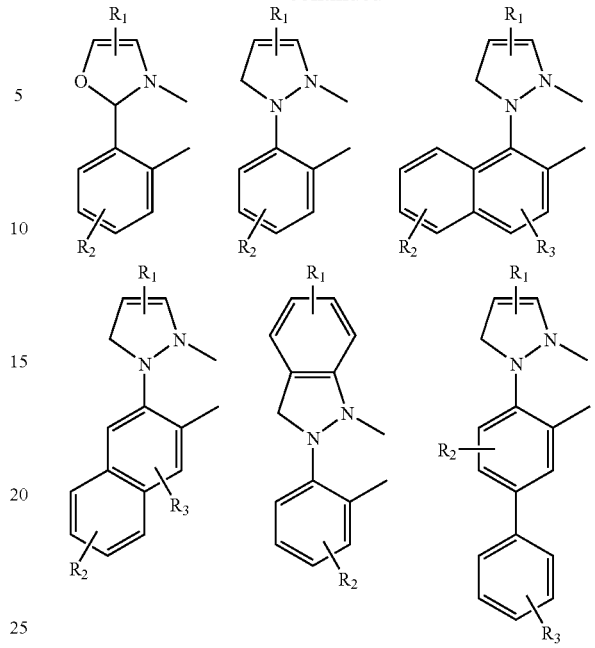

where Z is S, O, or NR$_8$; and

R$_1$, R$_2$, R$_3$, R$_4$, R$_5$, R$_6$, R$_7$, and R$_8$ are each independently hydrogen, halogen, OH, CF$_3$, CN, silyl, alkyl, aryl, alkoxy, aryloxy, amino, or arylene, wherein adjacent Rs may be fused together to form a five to seven membered aliphatic or aromatic ring.

In R$_1$ through R$_8$, the alkyl group may have 1 to 30 carbon atoms, the aryl group may have 5 to 30 carbon atoms, the alkoxy group may have 1 to 30 carbon atoms, the aryloxy group may have 5 to 30 carbon atoms, and the arylene group may have 2 to 30 carbon atoms.

In the cyclometalated transition metal complex of Formula 1, the second mono anionic bidentate chelating ligand can be preferably selected from ligands represented by formulae below:

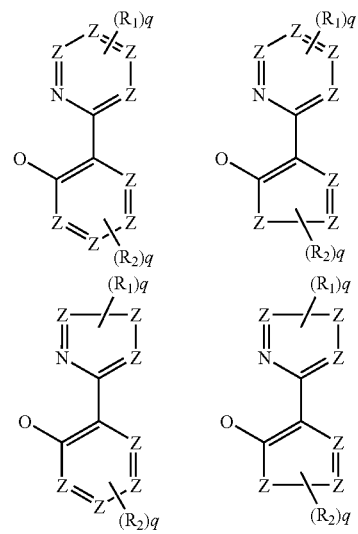

where Z is C, N, O, S, or P;
q is an integer from 0 to 5; and
R$_1$ and R$_2$ are each independently hydrogen, halogen, OH, CF$_3$, CN, silyl, alkyl, aryl, alkoxy, aryloxy, amino, or arylene, wherein adjacent Rs may be fused together to form a five- to seven- membered aliphatic or aromatic ring.

In $R_1$ and $R_2$, the alkyl group may have 1 to 30 carbon atoms, the aryl group may have 5 to 30 carbon atoms, the alkoxy group may have 1 to 30 carbon atoms, the aryloxy group may have 5 to 30 carbon atoms, and the arylene group may have 2 to 30 carbon atoms.

Preferably, the second mono anionic bidentate chelating ligand can be selected from ligands represented by formulae below:

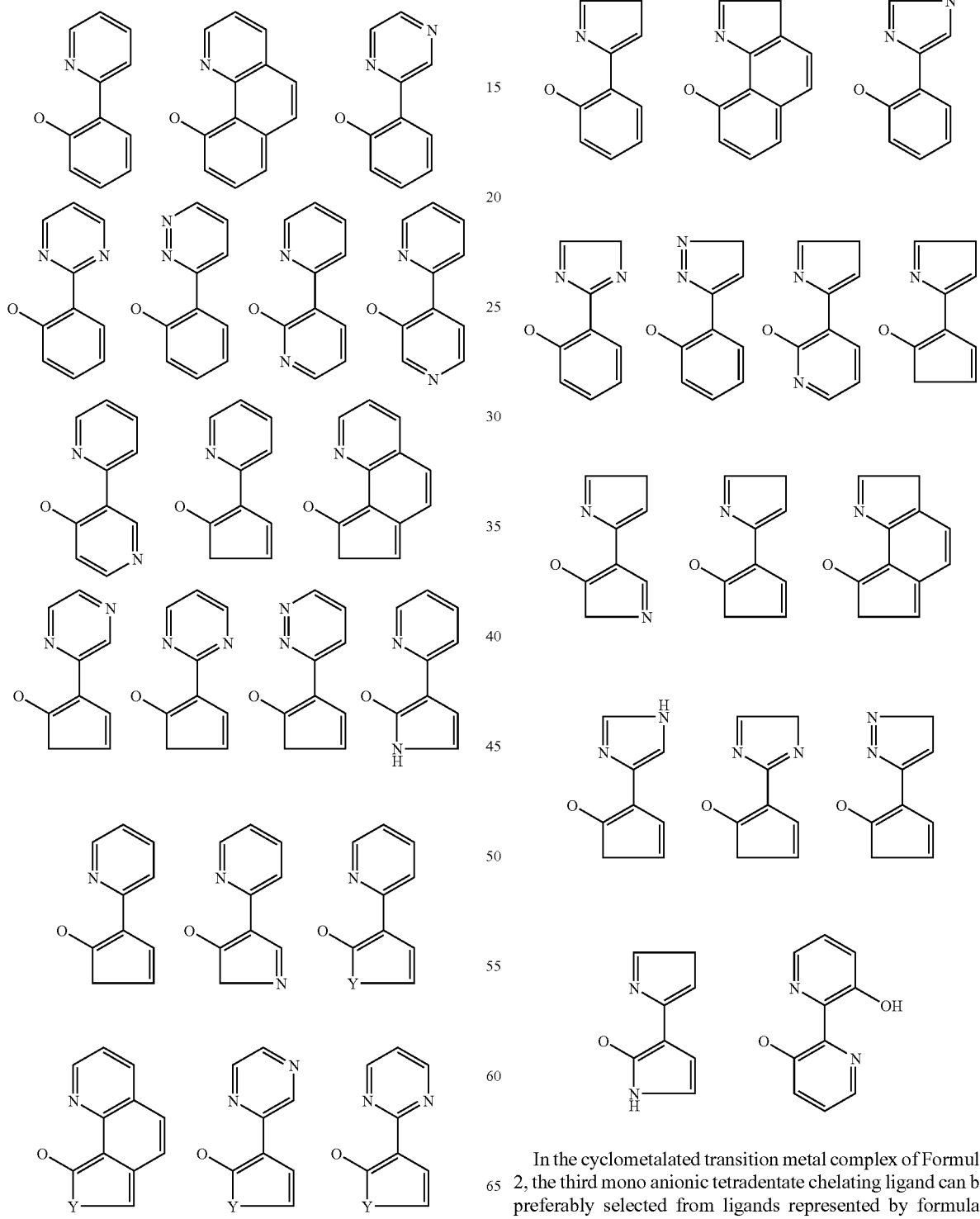

In the cyclometalated transition metal complex of Formula 2, the third mono anionic tetradentate chelating ligand can be preferably selected from ligands represented by formulae below:

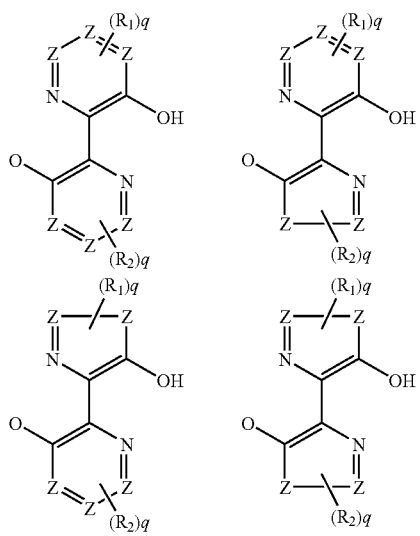

where Z is C, N, O, S, or P;
q is an integer from 0 to 5; and
$R_1$ are $R_2$ are each independently hydrogen, halogen, OH, $CF_3$, CN, silyl, alkyl, aryl, alkoxy, aryloxy, amino, or arylene, wherein adjacent Rs may be fused together to form a five- to seven- membered aliphatic or aromatic ring.

In $R_1$ and $R_2$, the alkyl may have 1-30 carbons, the aryl may have 5-30 carbons, the alkoxy may have 1-30 carbons, the aryloxy may have 5-30 carbons, and the arylene may have 2-30 carbons.

In the cyclometalated transition metal complex of Formula 3, the di-anionic tetradentate chelating ligand can be preferably selected from ligands represented by formulae below:

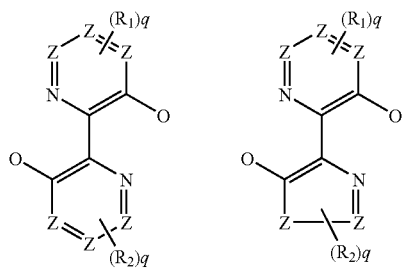

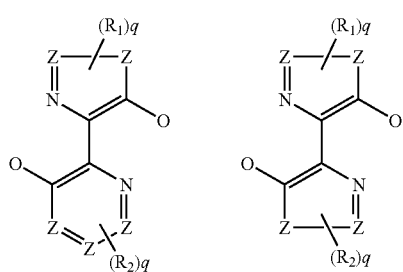

where Z is C, N, O, S, or P; q is an integer from 0 to 5; and $R_1$ and $R_2$ are each independently hydrogen, halogen, $CF_3$, CN, silyl, alkyl, aryl, alkoxy, aryloxy, amino, or arylene, wherein adjacent Rs may be fused together to form a five to seven membered aliphatic or aromatic ring.

In $R_1$ and $R_2$, the alkyl may have 1-30 carbons, the aryl may have 5-30 carbons, the alkoxy may have 1-30 carbons, the aryloxy may have 5-30 carbons, and the arylene may have 2-30 carbons.

Preferably, in the cyclometalated transition metal complex of Formula 3, the di-anionic tetradentate chelating ligand can be selected from ligands represented by formulae below:

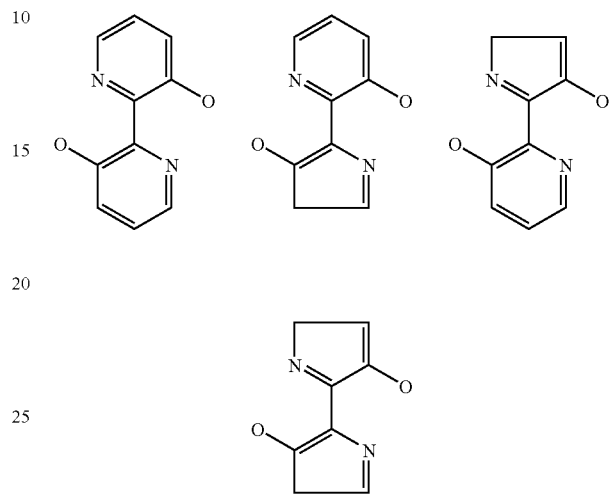

In the cyclometalated transition metal complexes of Formulae 1 through 3, M is preferably Ru, Rh, Os, Ir, Pt, or Au.

More preferably, in the cyclometalated transition metal complexes of Formulae 1 through 3, M is Ir.

Preferably, the cyclometalated transition metal complex of Formula 1 or Formula 2 can be a complex represented by one of formulae 4 through 8:

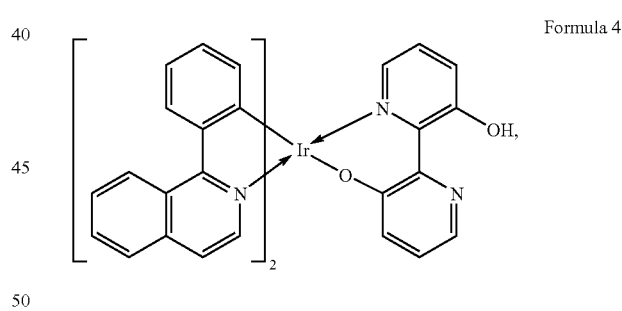

Formula 4

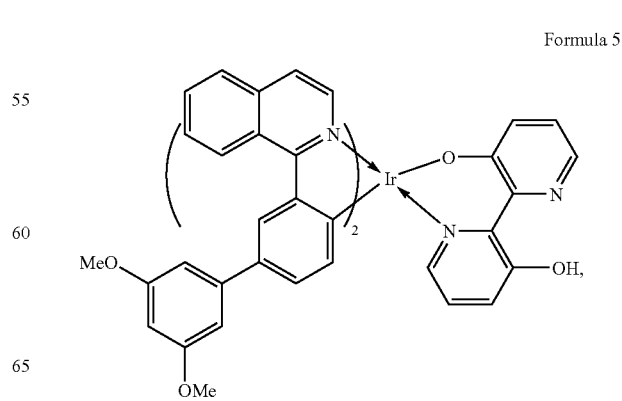

Formula 5

-continued

Formula 6

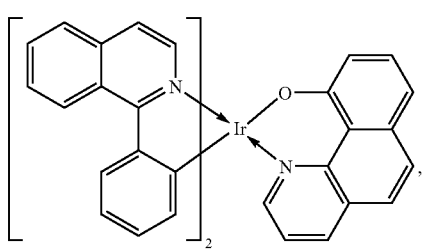

Formula 7

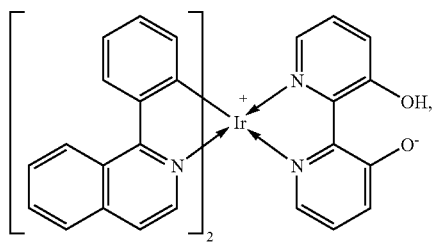
and

Formula 8

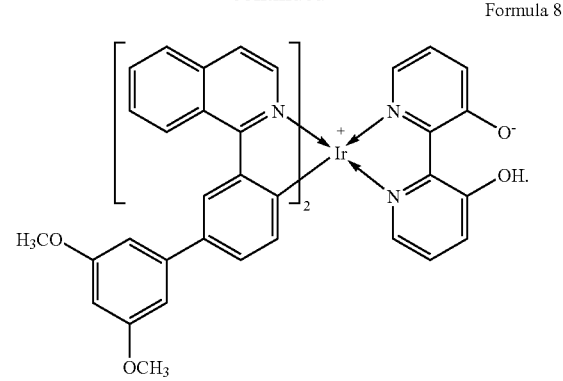

The complex of Formula 4 is an isomer of the complex of Formula 7 and vice versa. The complex of Formula 5 is an isomer of the complex of Formula 8 and vice versa. That is, the complex of Formulae 4, 5, 7, and 8 can be represented by

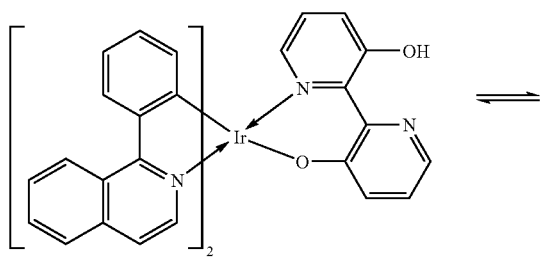 ⇌ 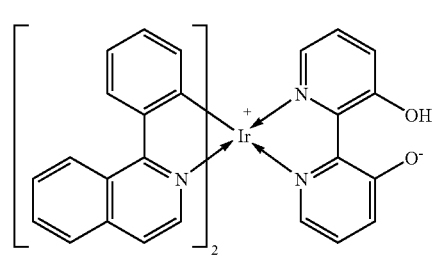

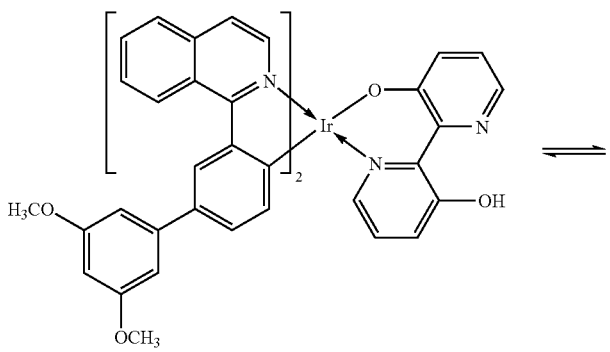 ⇌ 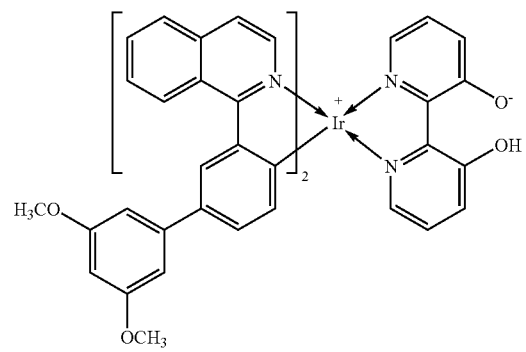

The cyclometalated transition metal complex of Formula 3 can be a complex represented by one of formulae 9 and 10 below:

Formula 9

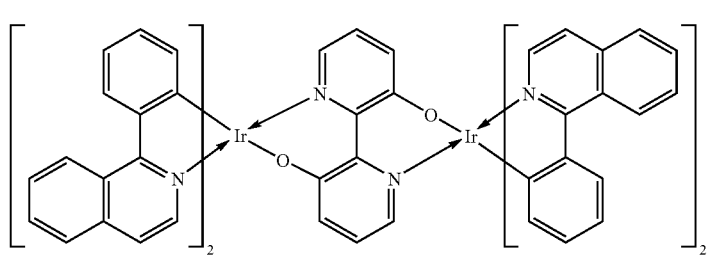

Formula 10

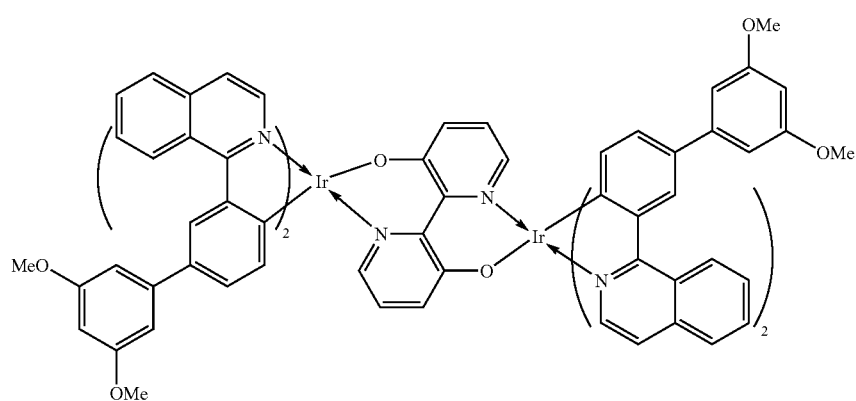

The cyclometalated transition metal complexes according to embodiments of the present invention can emit light of wavelengths between 500 nm and 670 nm.

The cyclometalated transition metal complexes according to embodiments of the present invention can be prepared using various methods. For example, when M is Ir, a [Ir(CY1)(CY2)Cl]$_2$ derivative can be used as a starting material in a method developed by Watts group (F. O. Garces, R. J. Watts, Inorg. Chem. 1988, (35), 2450 which is incorporated herein by reference) to prepare a cyclometalated transition metal complex.

Hereinafter, a process of synthesizing a transition metal complex containing bipyridinediol ligand that is an example of the cyclometalated transition metal complex of Formula 1 according to an embodiment of the present invention will be described.

Referring to Reaction Scheme 1 below, a [Ir(CY1)(CY2)Cl]$_2$ derivative and a sodium salt of 2,2-bipyridine-3,3-diol are added to a mixture solution of chloroform and methanol in a ratio of 3:1, and then stirred at a temperature of 30 to 50° C. for 18 hours. As a result, a cyclometalated transition metal complex according to an embodiment of the present invention can be synthesized.

Reaction Scheme 1

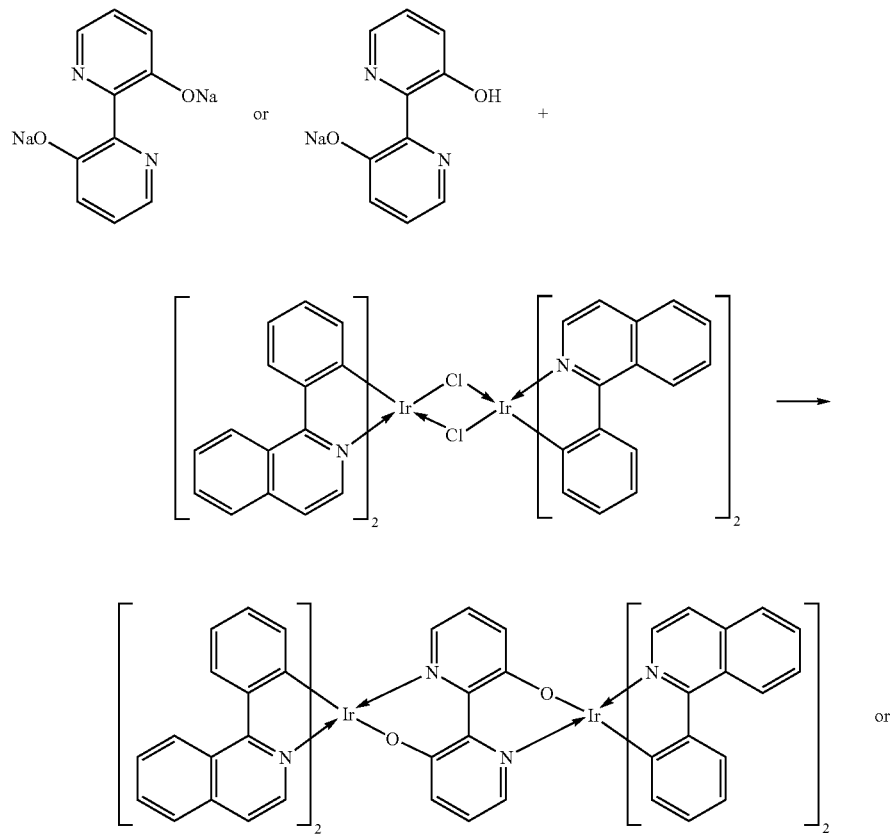

-continued

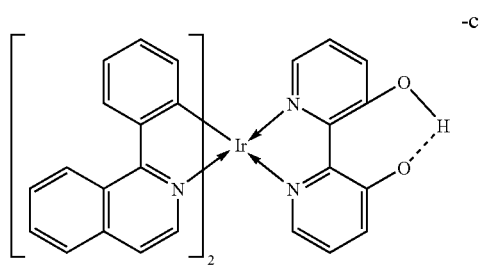 or 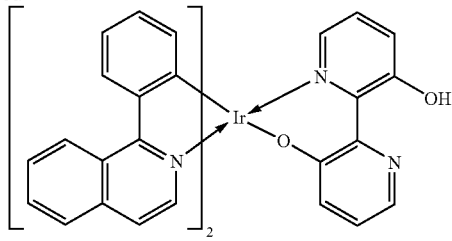

An organic light emitting device according to an embodiment of the present invention includes an organic layer interposed between a pair of electrodes (a first electrode and a second electrode), wherein the organic layer contains the cyclometalated transition metal complex prepared above.

The cyclometalated transition metal complexes of Formulae 1 through 3 are very useful as a phosphor dopant that is used to form an emission layer which shows high luminous efficiency in a red light wavelength region.

When a cyclometalated transition metal complex is used as a phosphor dopant in an organic light emitting device, the organic layer may further contain at least one material selected from one or more kinds of polymer host, a mixture of a polymer host and a low molecular weight host, a low molecular weight host, and a non-emission polymer matrix.

The polymer host, the low molecular weight host, and the non-emission polymer matrix can be any polymer host, any low molecular weight host, and any non-emission polymer matrix that are commonly used in an emission layer of an organic light emitting device. Examples of the polymer host are PVK(polyvinylcarbazole), polyfluorene etc. Examples of the low molecular weight host are CBP(4,4'-N,N'-dicarbazole-biphenyl), 4,4'-bis[9-(3,6-biphenylcarbazolyl)]-1,1'-biphenyl, 9,10-bis[(2',7'-t-butyl)-9',9"-spirobifluorenylanthracene, tetrafluorene, etc. Examples of the non-emission polymer matrix are polymethylmethacrylate, polystyrene, etc. However, the polymer host, the molecular weight host, and the non-emission matrix are not limited thereto.

The content of the cyclometalated transition metal complex may be in the range of 1 to 30 parts by weight based on 100 parts by weight of the total weight of materials that are used to form an emission layer. The cyclometalated transition metal complex can be used to form an emission layer by vacuum depositing, sputtering, printing, coating, injecting, electron beaming, or the like.

In the organic light emitting device, the organic layer may further contain a green light emitting material or a blue light emitting material. When the organic layer further contains both green and blue emission materials, white light can be obtained.

The thickness of the organic layer may be in the range of 10 to 1000 nm. The organic layer refers to a layer formed of an organic material interposed between a pair of electrodes of an organic light emitting device. Such a layer can be, in addition to an emission layer, an electron transport layer, a hole transport layer, etc.

The organic light emitting device according to an embodiment of the present invention can be manufactured according to a conventional process of manufacturing an organic light emitting device without specific apparatuses and methods.

The organic light emitting device according to an embodiment of the present invention may have various structures. The organic light emitting device can further include, interposed between a pair of electrodes, at least one layer selected from a buffer layer, a hole injection layer, a hole transport layer, an electron blocking layer, a hole blocking layer, an electron transport layer, and an electron injection layer.

Figure 1B:
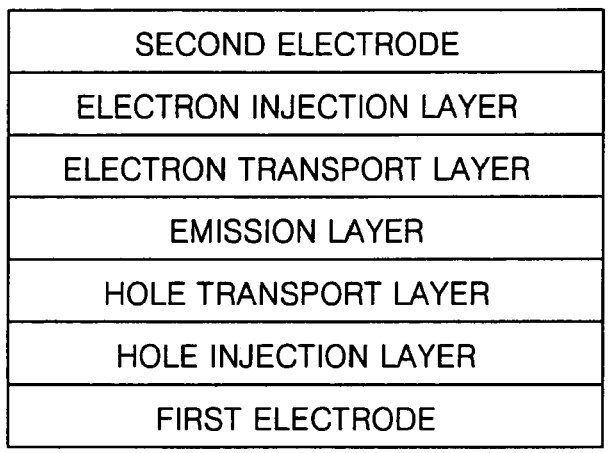
Figure 1C:
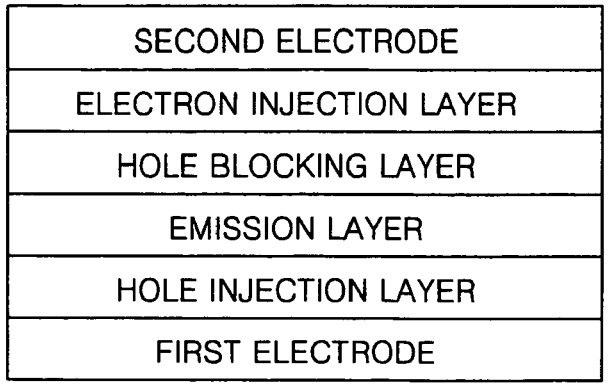

Organic electroluminescent devices according to embodiments of the present invention are illustrated in FIGS. 1A, 1B, and 1C. FIG. 1A is a sectional view of an organic light emitting device that includes a first electrode/hole injection layer/emission layer/electron transport layer/electron injection layer/second electrode structure. FIG. 1B is a sectional view of an organic light emitting device that includes a first electrode/hole injection layer/hole transport layer/emission layer/electron transport layer/electron injection layer/second electrode structure. FIG. 1C is a sectional view of an organic light emitting device that includes a first electrode/hole injection layer/emission layer/hole blocking layer/electron injection layer/second electrode structure. In these organic light emitting devices, the emission layer can include the cyclometalated transition metal complex according to an embodiment of the present invention. The emission layer of an organic light emitting device according to an embodiment of the present invention can contain a phosphor or fluorescent dopant for realizing green, blue, or white light.

Hereinafter, a method of manufacturing an organic light emitting device according to an embodiment of the present invention will be described in detail with reference to the organic light emitting device illustrated in FIG. 1C.

First, a large work function material that is used to form a first electrode is deposited or sputtered on a substrate to form a first electrode. The first electrode can act as an anode. The substrate can be any substrate that is used in a conventional organic light emitting device. For example, the substrate can be a glass substrate or a transparent plastic substrate, both of which have excellent mechanical strength, thermal stability, transparency, and surface smoothness, can be easily handled, and are waterproof. A material that is used to from the first electrode can be a transparent, conductive metal, such as Indium tin oxide (ITO), Indium zinc oxide (IZO), tin oxide ($SnO_2$), zinc oxide (ZnO), and the like.

Then, a hole injection layer (HIL) can be formed on the first electrode by vacuum deposition, spin coating, casting, Langmuir-Blodgett (LB), or the like.

When the HIL is formed by vacuum deposition, deposition conditions may vary according to a material that is used to form the HIL and structural and thermal properties of a HIL that will be formed. In general, however, the deposition temperature may be in the range of 100 to 500° C., a degree of vacuum may be in the range of $10^{-8}$ to $10^{-3}$ torr, a vacuum speed may be in the range of 0.01 to 100 Å/sec, and a thickness of a layer may be in the range of 10 Å to 5 μm.

When the HIL is formed by spin coating, coating conditions may vary according to a material that is used to form the HIL and desired structural and thermal properties of the HIL that will be formed. In general, however, a coating speed may be in the range of about 2,000 rpm to 5,000 rpm, and a temperature for a heat treatment that is performed to remove the used solvent after coating may be in the range of about 80° C. to 200° C.

A material that is used to form the HIL is not limited, and can be a phthalocyanine compound, such as copper phthalocyanine disclosed in U.S. Pat. No. 4,356,429; a starburst type amine derivative, such as TCTA, m-MTDATA, or m-MTDAPB, disclosed in Advanced Material, 6, p. 677(1994), or a soluble conductive polymer, such as Pani/DBSA (polyaniline/dodecylbenzenesulfonic acid), PEDOT/PSS (poly(3, 4-ethylenedioxythiophene)/poly(4-styrenesulfonate), Pani/CSA (polyaniline/camphor sulfonic acid), or PANI/PSS (polyaniline)/poly(4-styrenesulfonate).

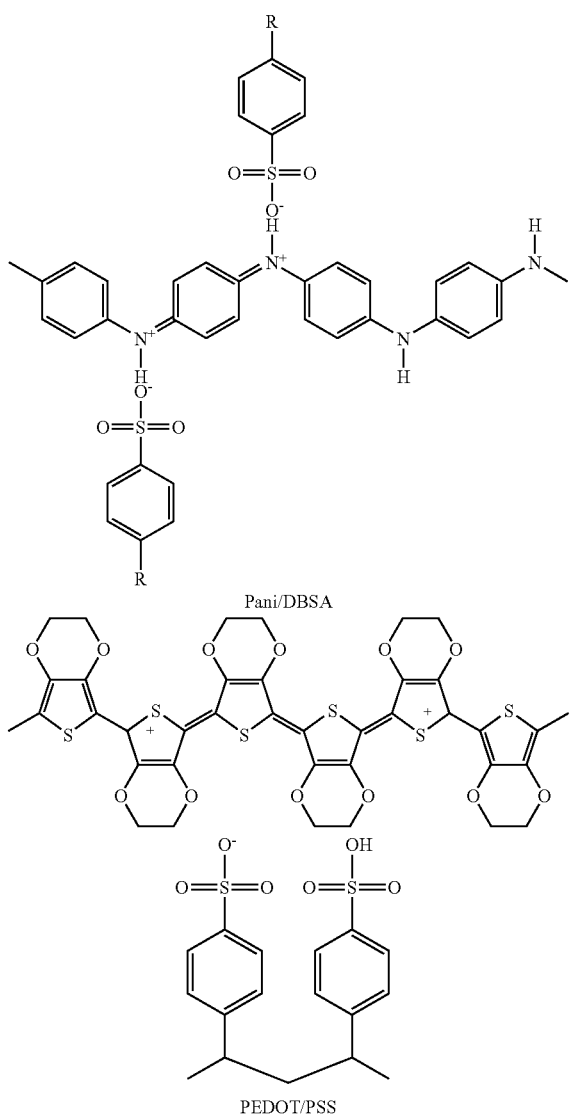

A thickness of the HIL may be in the range of about 100 Å to 10,000 Å, preferably 100 Å to 1,000 Å. When the thickness of the HIL is less than 100 Å, a hole injection property may decrease. On the other hand, when the thickness of the HIL is more than 10000 Å, the operating voltage of the device may increase.

Then, an emission layer (EML) can be formed on the HIL by vacuum depositing, spin coating, casting, LB, or the like. When the EML is formed by vacuum depositing or spin coating, formation conditions may vary according to a material that is used to form the EML. In general, however, the EML may be formed under similar conditions as in a process of forming the HIL.

The EML can be formed using an arylene-based derivative having a polar functional group of Formula 1 as described above. At this time, a soluble compound can be used together with an organic semiconductor. The organic semiconductor can be pentacene, polythiophene, tetrathiafulvalene, or the like.

The arylene-based derivative of Formula 1 can be used with an appropriate host material that is known in the art. The host material can be Alq$_3$, CBP(4,4'-N,N'-dicarbazole-biphenyl), PVK(poly(n-vinylcarbazole)), or the like.

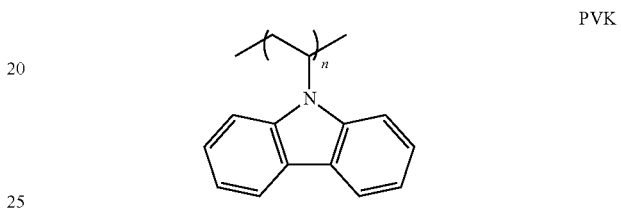

There are various dopants that are known that can be used to form an EML, in addition to the aminostyryl compound used in the embodiments of the present invention. For example, a fluorescent dopant can be IDE102 or IDE105 that is commercially available from Idemitsu Inc, or C545T that is commercially available from Hayashibara Inc., and a phosphor dopant can be PtOEP (Pt octaethyl porphyrin) that is a red phosphor dopant, RD 61 that is available from UDC Inc., Ir(PPy)$_3$(PPy=2-phenylpyridine) that is a green phosphor dopant, F2Irpic (bis[2-(4,6-difluorophenyl)pyridinato-N, C2'] iridium picolinate) that is a blue phosphor dopant, RD 61 that is a red phosphor dopant available from UDC Inc., or the like.

A concentration of the dopant is not limited, and may be in the range of 0.01 to 15 parts by weight based on 100 parts by weight of a host.

The thickness of the EML may be in the range of about 100 Å to 1,000 Å, preferably 200 Å to 600 Å. When the thickness of the emission layer is less than 100 Å, the luminous efficiency may decrease. On the other hand, when the thickness of the emission layer is more than 1,000 Å, the operating voltage may increase.

When the EML is formed with a phosphor dopant, a hole blocking layer (HBL) can be formed on the EML by vacuum depositing, spin coating, casting, LB, or the like, to prevent diffusion of triplet excitons or holes into an electron injection layer. When the HBL is formed by vacuum depositing or spin coating, formation conditions may vary according to a compound that is used to form the HBL. In general, however, the HBL is formed under similar conditions as when the HIL is formed. A known material that is used to form the HBL can be an oxadiazole derivative, a triazole derivative, phenanthroline derivative, or BCP (2,9-dimethyl-4,7-diphenyl-1,10-phenanthroline) disclosed in JP 11-329734(A1) as a hole blocking material.

A thickness of the HBL may be in the range of 50 Å to 1,000 Å, preferably 100 Å to 300 Å. When the thickness of the HBL is less than 50 Å, the hole blocking property may decrease. On the other hand, when the thickness of the HBL is more than 1000 Å, the operating voltage of the device may increase.

A material that allows electrons to be easily injected from the anode can be deposited on the HBL to form an electron injection layer (EIL), and is not limited.

The EIL can be formed using a known material that is known in the art, such as LiF, NaCl, CsF, Li$_2$O, Ba, or the like. Formation conditions for the EIL may vary according to a material that is used to form EIL. In general, however, the EIL can be formed under similar conditions as when the HIL is formed.

A thickness of the EIL may be in the range of about 1 Å to 100 Å, preferably 5 Å to 50 Å. When the thickness of the EIL is less than 1 Å, the electron injection property may decrease. On the other hand, when the thickness of the EIL is more than 100 Å, the operating voltage of the device may increase.

Then, a second electrode can be formed on the EIL by vacuum depositing or sputtering. The second electrode can act as a cathode. A metal that is used to form the second electrode may be a low work function metal, an alloy, an electrically conductive compound, or a mixture of these. For example, the metal that is used to form the second electrode can be Li, Mg, Al, Al—Li, Ca, Mg—In, Mg—Ag, or the like. Meanwhile, in order to obtain a top emission type display device, a transparent cathode formed of ITO or IZO can be used.

Organic electroluminescent devices according to embodiments of the present invention can have various structures, in addition to the first electrode/hole injection layer(HIL)/emission layer (EML)/hole blocking layer (HBL)/electron injection layer/second electrode structure illustrated in FIG. 1C. In addition, these layers may not be used when needed.

For example, a buffer layer, a hole transport layer, and an electron transport layer can be further added.

A material that is used to form a buffer layer can be any material that is commercially used, and can be copper phthalocyanine, polythiophene, polyaniline, polyacetylene, polypyrrole, polyphenylenevinylene, or derivatives of these. However, the material that is used to form a buffer layer is not limited thereto.

A hole transport layer (HTL) can be formed on the HIL by vacuum depositing, spin coating, casting, LB, or the like. When the HTL is formed by vacuum depositing or spin coating, deposition conditions and coating conditions may vary according to a material that is used to from the HTL. In general, however, the HTL can be formed under similar conditions as when the HIL is formed.

A material that is used to form the HTL is not limited, and can be any known material that is used to form a HTL. For example, the material that can be used to form the HTL may be a carbazole derivative, such as N-phenylcarbazole or polyvinylcarbazole or an amine derivative having an aromatic fused ring, such as N,N'-bis(3-methylphenyl)-N,N'-diphenyl-[1,1-biphenyl]-4,4'-diamine(TPD), N,N'-di(naphthalene-1-yl)-N,N'-diphenyl benzidine (α-NPD), or the like.

A thickness of the HTL may be in the range of about 50 Å to 1,000 Å, preferably 100 Å to 600 Å. When the thickness of the HTL is less than 50 Å, the hole transporting property may decrease. On the other hand, when the thickness of the HTL is more than 1,000 Å, the operating voltage of the device may increase.

The ETL can be formed by vacuum depositing, spin coating, casting, or the like. When the ETL is formed by vacuum depositing or spin coating, formation conditions may vary according to a material that is used to form an ETL. In general, however, the ETL can be formed under similar conditions as when the HIL is formed. The material that is used to form the ETL stably transports electrons injected from an electron injection electrode (cathode), and can be polyoxadiazole, a quinoline derivative, such as tris(8-quinolinolate) aluminum (Alq$_3$), TAZ, or the like.

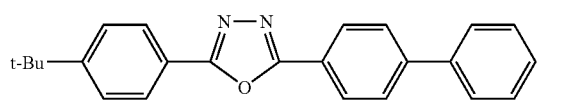

TAZ

A thickness of the ETL may be in the range of about 100 Å to 1,000 Å, preferably 200 Å to 500 Å. When the thickness of the ETL is less than 100 Å, the electron transport property may decrease. On the other hand, when the thickness of the ETL is more than 1,000 Å, the operating voltage of the device may increase.

The cyclometalated transition metal complexes according to embodiments of the present invention can emit light having wavelengths of between 500 to 670 nm. Emitting diodes using such organic metal complexes can be used in a light source for full-color displays, back lights, billboards, optical communications, and interior decorations.

The cyclometalated transition metal complexes of Formulae 1 through 3 are prepared using a conventional organic synthesis method. The synthesized complexes were identified using a 1H NMR and a Mass spectrometer.

Hereinafter, Complexes 4 through 11 represented by Formulae 4 through 11 (hereinafter, referred to as Complex 4 through Complex 11, respectively) will be described as prepared according to Synthesis Examples and Examples, but the present invention is not limited to these Synthesis Examples and Examples.

SYNTHESIS EXAMPLE

Synthesis Example 1

Synthesis of Piq dimer

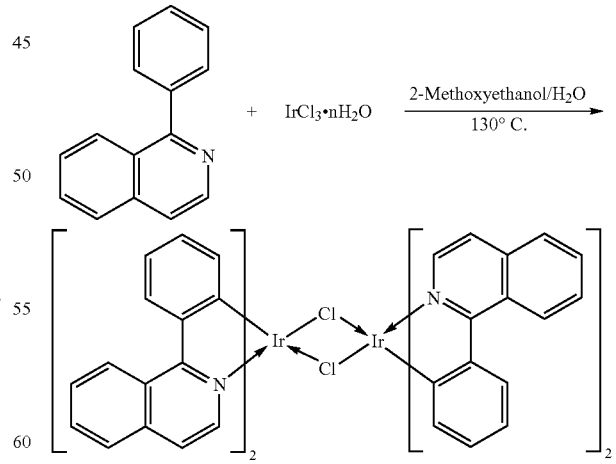

Piq dimer ([Ir(Piq)$_2$Cl]$_2$) that is red powder was synthesized using 2-phenylisoquinoline ligand and IrCl$_3$.nH$_2$O. A synthesis method disclosed in J. Am. Chem. Soc., 1984, 106, 6647-6653 which is incorporated herein by reference was used.

Synthesis Example 2
Synthesis of 2-[3-(3,5-dimethoxyphenyl)-1-phenyl]isoquinoline (DMPPiq) dimer Reaction Scheme 3

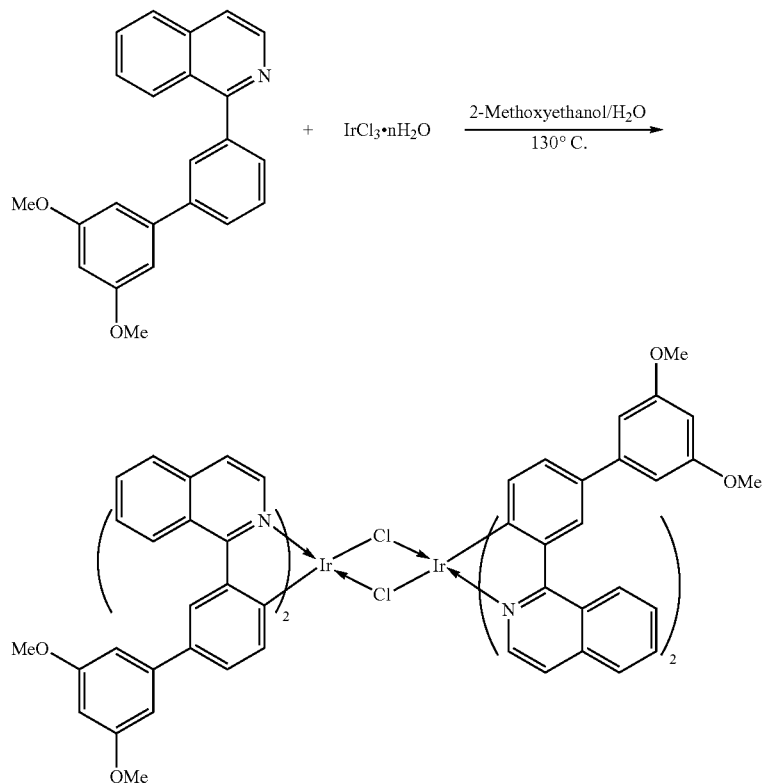

2-[3-(3,5-dimethoxyphenyl)-1-phenyl]-isoquinoline dimer [Ir(DMPPiq)$_2$Cl]$_2$ that is red powder was synthesized using 2-[3-(3,5-dimethoxyphenyl)-1-phenyl]-isoquinoline ligand that was synthesized through Suzuki Coupling and IrCl$_3$.nH$_2$O. A synthesis method disclosed in J. Am. Chem. Soc., 1984, 106, 6647-6653 was used.

EXAMPLES
Example 1
Synthesis of Complex 7 and Complex 9 Respectively Represented by Formula 7 and Formula 9

Formula 7

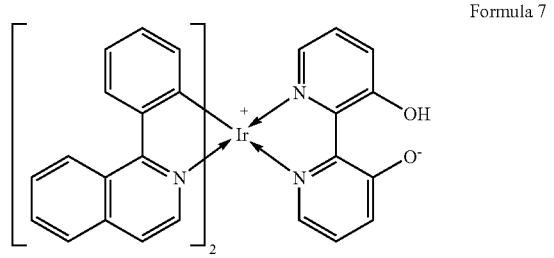

Formula 9

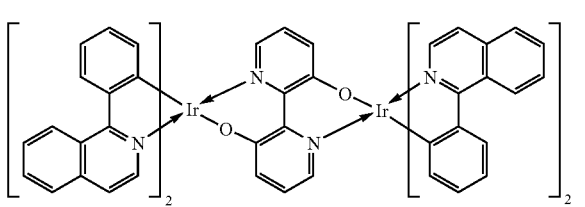

Figure 2:
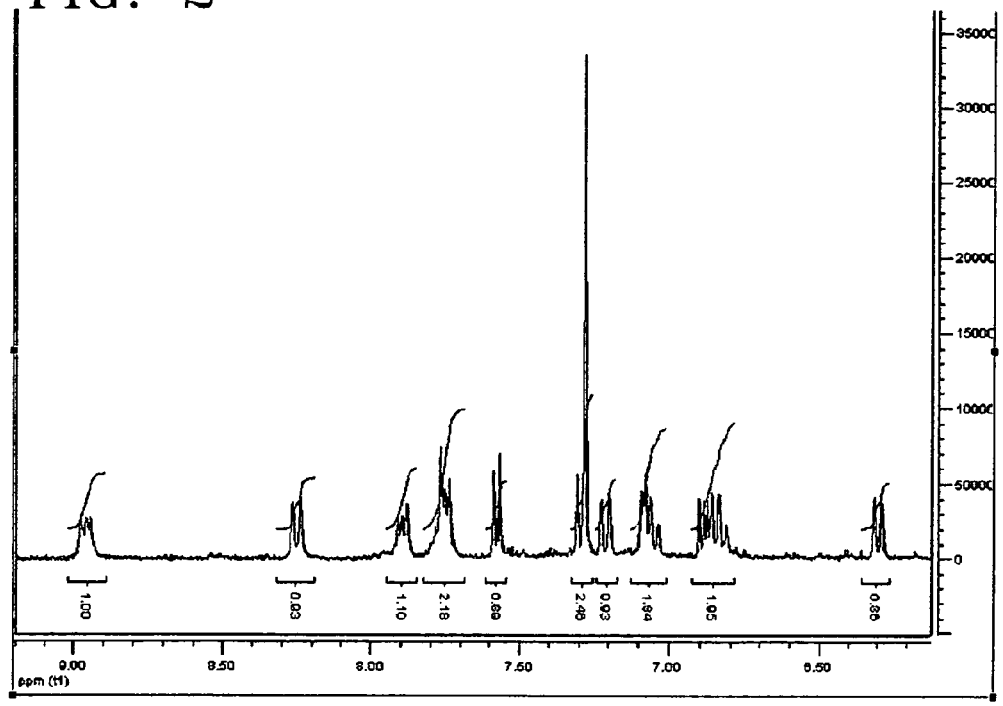
FIG. 2 is a graph showing results of a $^1$H NMR experiment on Complex 7 according to an embodiment of the present invention.
Figure 6:
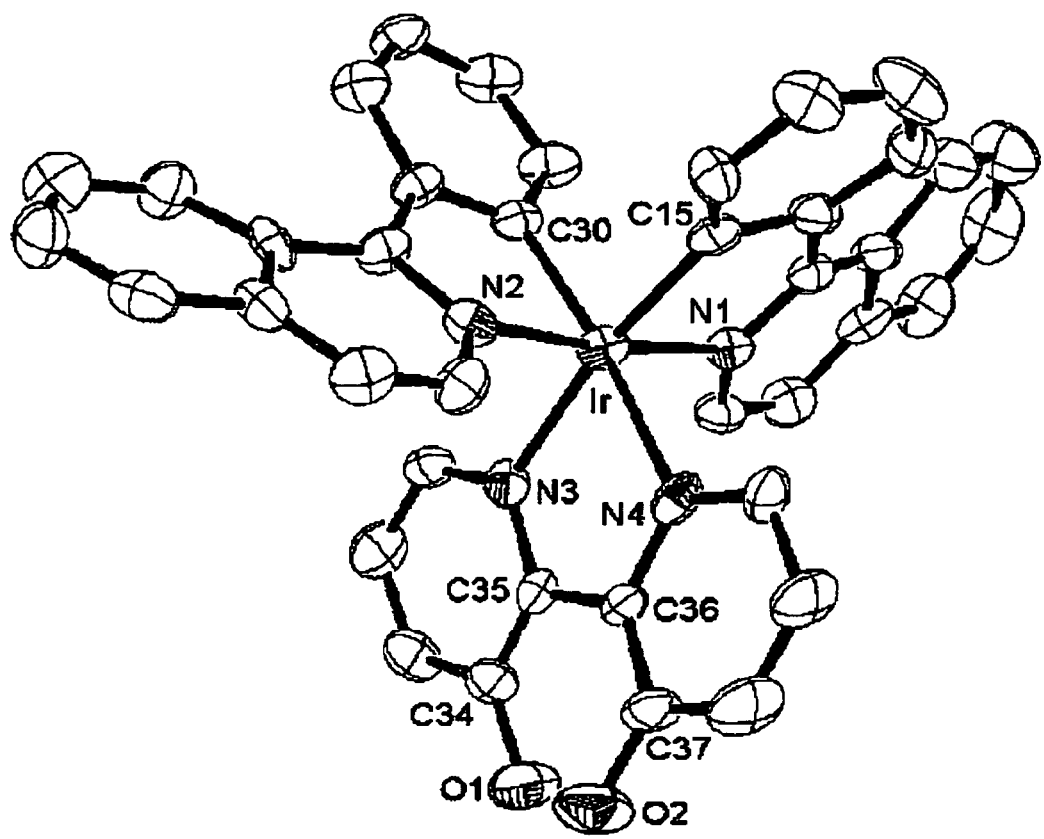
FIG. 6 is a graph showing results of an X-ray single crystal analysis of Complex 7 according to an embodiment of the present invention.

635 mg (0.5 mmol) of [(Piq)$_2$IrCl]$_2$ prepared according to Synthesis Example 1 and 250 mg (1.2 mmol) of a sodium salt of 2,2-bipyridine-3,3-diol that had been prepared by treating 2,2-bipyridine-3,3-diol with NaOH in a methylenechloride/methanol solvent were dissolved in a chloroform solution in a 100 ml two-neck flask with a thermometer, a mechanical agitator, and a reflux condenser in a nitrogen atmosphere and then reacted at 50° C. for 18 hours. When the reaction was completed, the reaction product was cooled to room temperature and then the solvent used was removed in a vacuum. A residual solid was dissolved in chloroform, and then the dissolved portion of the residual solid was filtered. Then, the filtrate was purified and isolated using column chromatography. The eluent used was a solution of chloroform and methanol in a ratio of 10:1. The final products yielded were red Complex 7 and orange Complex 9, and respective yields thereof were 30% and 10%. Complex 7 and Complex 9 were identified using $^1$H NMR. FIG. 2 is a graph showing the result of $^1$H NMR of Complex 7. FIG. 6 is a graph showing results of an X-ray crystal structure analysis of Complex 7.

$^1$H-NMR(CDCl$_3$, ppm) of Complex 7: 8.96[m, 2H], 8.28 [d, 2H], 7.91[m, 2H], 7.76[m, 4H], 7.60[d, 2H], 7.33[d, 2H], 7.07[m, 4H], 6.83[m, 4H], 6.29[dd, 2H]

Example 2

Synthesis of Complex 8 and Complex 10 Respectively Represented by Formula 8 and Formula 10

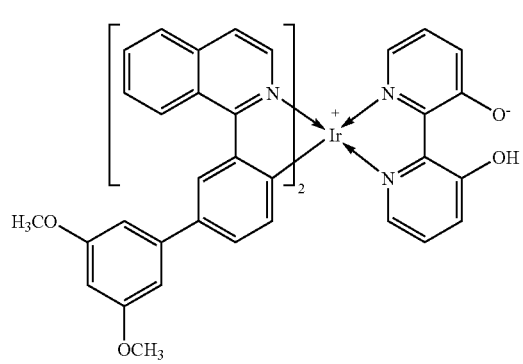

Formula 8

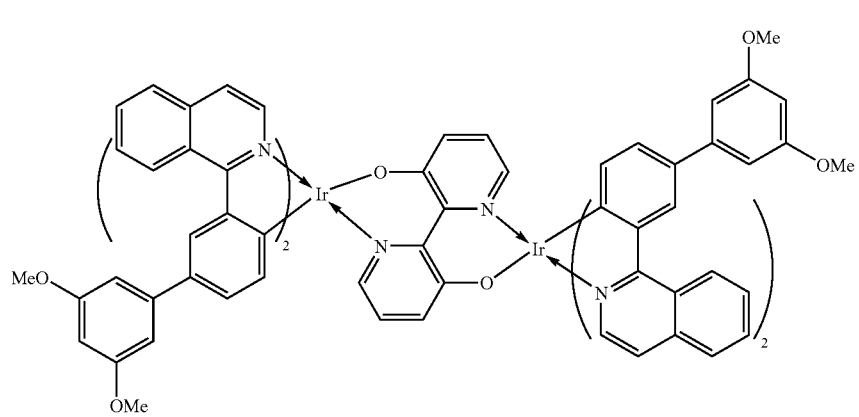

Formula 10

836 mg (0.5 mmol) of ([Ir(DMPPiq)$_2$Cl]$_2$) prepared according to Synthesis Example 2 and 250 mg (1.2 mmol) of a sodium salt of 2,2-bipyridine-3,3-diol that had been prepared by treating 2,2-bipyridine-3,3-diol with NaOH in a methylenechloride/methanol solvent were dissolved in a chloroform solution in a 100 ml two-neck flask with a thermometer, a mechanical agitator, and a reflux condenser in a nitrogen atmosphere and then reacted at 50° C. for 18 hours. When the reaction was completed, the reaction product was cooled to room temperature and then the solvent used was removed in a vacuum. The residual solid was dissolved in chloroform and then the portion of the residual solid that did not dissolve was filtered. Then, the filtrate was purified and isolated using column chromatography. The eluent used was a solution of chloroform and methanol in a ratio of 10:1. The final products were red Complex 8 and orange Complex 10, and respective yields thereof were 30% and 10%.

$^1$H-NMR(CDCl$_3$, ppm) of Complex 4: 9.11[d, 1H], 9.05[d, 1H], 8.93[d, 1H], 8.56[m, 2H], 8.30[d, 1H], 7.89[m, 1H], 7.76~7.64 [m, 6H], 7.39[d, 1H], 7.23[d, 1H], 7.01[dd, 1H], 6.87[m, 2H], 6.77[d, 2H], 6.61[d, 2H], 6.55[dd, 1H], 6.43[t, 1H], 6.35[t, 1H], 6.20[dd, 1H], 6.12[d, 1H], 5.61 [m, 1H]

Example 3

Synthesis of Complex 6 [Ir(Piq)2(hbq)] Represented by Formula 6

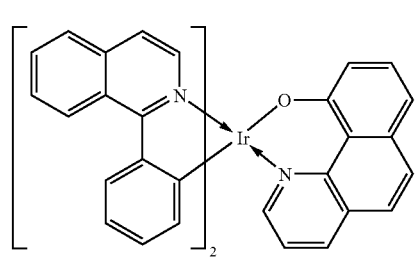

<Formula 6>

635 mg (0.5 mmol) of [(Piq)$_2$IrCl]$_2$ prepared according to Synthesis Example 1, 234 mg (1.2 mmol) of 10-hydoxybenzo[h]quinoline, and 345 mg (2.5 mmol) of potassium carbonate ($K_2CO_3$) were dissolved in a solution of chloroform and methanol in a ratio of 3:1 in a 100 ml two-neck flask with a thermometer, a mechanical agitator, and a reflux condenser in a nitrogen atmosphere, and then reacted at 50° C. for 18 hours. When the reaction was completed, the reaction product was cooled to room temperature and then the solvent used was removed in a vacuum. The residual solid was dissolved in chloroform and then the dissolved portion of the residual solid was filtered. Then, the filtrate was purified and isolated using column chromatography. The eluent used was a solution of chloroform and methanol in a ratio of 10:1. The final product was red Complex 6 and the yield thereof was 66%.

Comparative Example 1

Synthesis of Complex 11 ($Ir(Piq)_3$) Represented by Formula 11

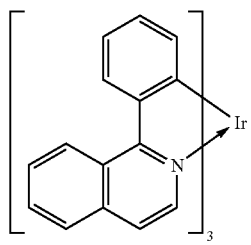

Formula 11

245 mg (0.5 mmol) of $Ir(acac)_3$ and 615 mg (3.0 mmol) of 2-phenylisoquinoline were dissolved in glycerol solution in a 100 ml two-neck flask with a thermometer, a mechanical agitator, and a reflux condenser in a nitrogen atmosphere, and then reacted at 200° C. for 26 hours. When the reaction was completed, the reaction product was cooled to room temperature and then water was added thereto to precipitate a solid. The resultant solution was filtered and the residual solid was washed with cold methanol and diethylether, and then dissolved in chloroform. The portion of the solid that was melted was refined using column chromatography. The eluent was a solution of chloroform and methanol in a mixture ratio of 10:1. The final product was red Complex 11 and the yield thereof was 43%.

Measurement Example 1

Luminous Properties of Complexes

Luminous properties of Complex 7 were determined by obtaining absorption spectrum and photoluminescence (PL) spectrum of Complex 3. First, Complex 7 was diluted with chloroform or dichloromethane ($CHCl_3$ or $CH_2Cl_2$) to obtain a solution having a concentration of 0.2 mM, and then the absorption spectrum of the diluted Complex 7 was measured using a shimadzu UV-350 spectrometer. Meanwhile, Complex 7 was diluted with chloroform or dichloromethane ($CHCl_3$ or $CH_2Cl_2$) to obtain a solution having a concentration of 10 mM, and then the PL spectrum of the diluted Complex 7 was measured using an ISC PC1 spectrofluorometer with a Xenon lamp. Results are shown in Table 1 and FIG. 3. The absorption spectra and PL spectra of Complexes 6, and 8 through 11 were measured in the same manner as described above.

Figure 3:
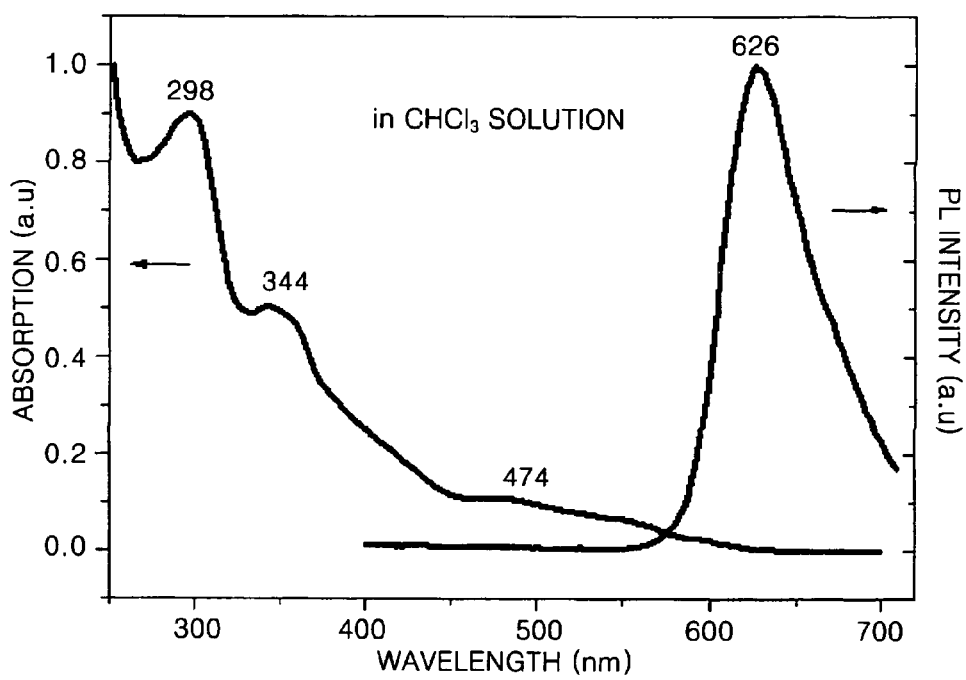
FIG. 3 is a graph showing results of UV and PL experiments on Complex 7 according to an embodiment of the present invention.
Figure 4:
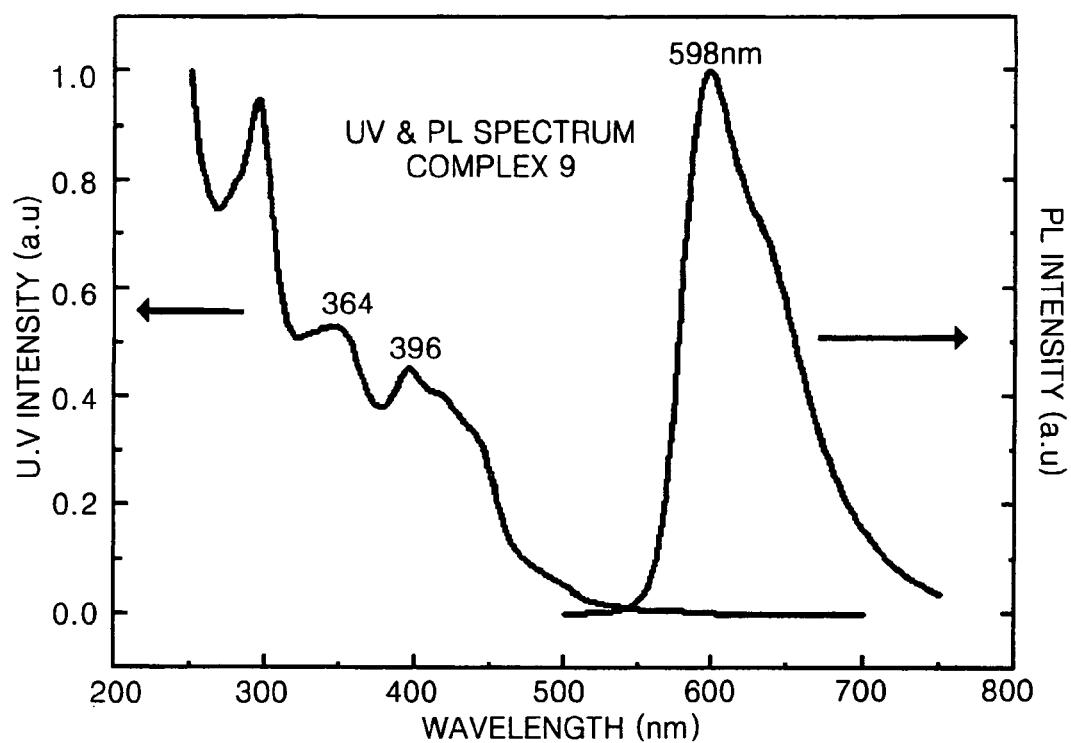
FIG. 4 is a graph showing results of UV and PL experiments on Complex 9 according to an embodiment of the present invention.
Figure 5:
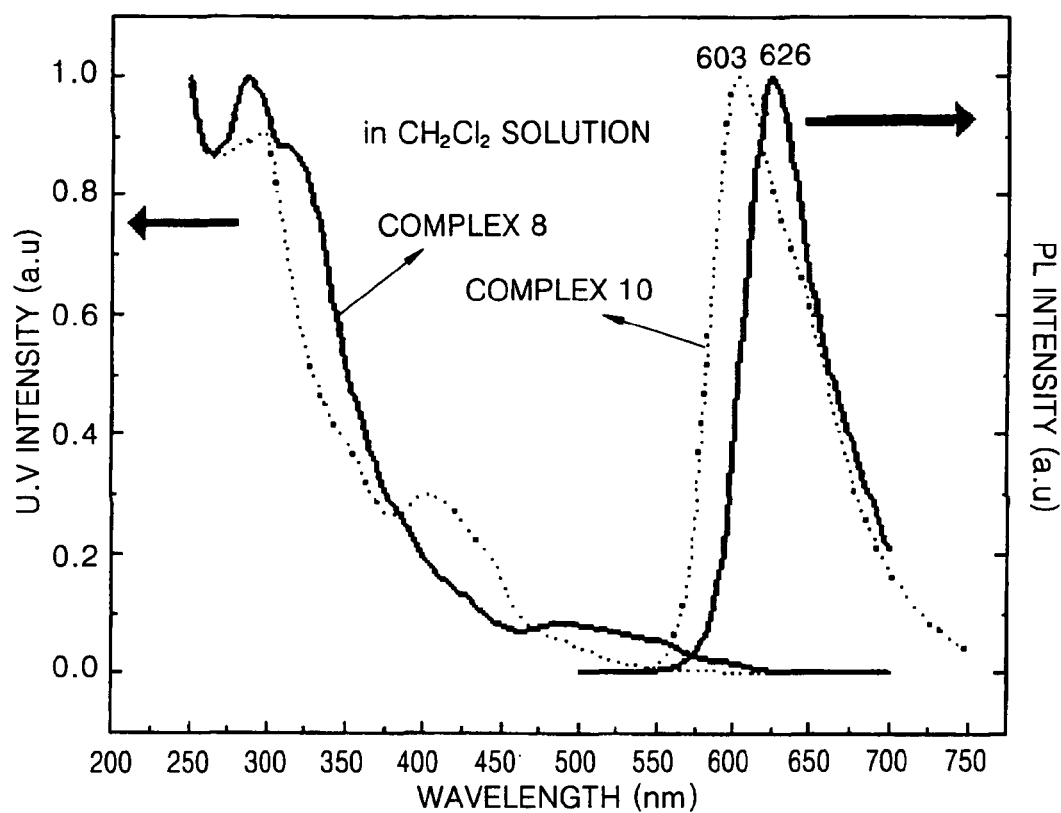
FIG. 5 is a graph showing results of UV and PL experiments on Complexes 8 and 10 according to an embodiment of the present invention.

The results are shown in Table 1, FIG. 3 (Complex 7), FIG. 4 (Complex 9), and FIG. 5 (Complexes 8 and 10).

TABLE 1

| Complex No. | Maximum Absorption Wavelength for MLCT (nm) | Maximum PL Wavelength (nm) |
| --- | --- | --- |
| 7 | 474 | 626 |
| 8 | 490 | 626 |
| 9 | 396 | 598 |
| 10 | 404 | 603 |
| 6 | 400 | 618 |
| 11 | — | 624 |

Measurement Example 2

Characteristics of Devices Manufacturing using the Complexes

An organic light emitting device having the following structure was manufactured using Complex 7 as a dopant of an emission layer: ITO/PEDOT (50 nm)/CBP+PVK+Complex7 (60 nm)/BAlq3 (30 nm)/LiF (0.8 nm)/Al (150 nm).

A 15 Å/$cm^2$ (1200 Å) ITO glass substrate that was produced by Corning Inc. was cut to a size of 50 mm×50 mm×0.7 mm, and then ultrasonically cleaned with isopropyl alcohol for 5 minutes, ultrasonically cleaned with pure water for five minutes, and then cleaned with UV ozone for 30 minutes. PEDOT-PSS (AI4083) produced by Bayer Inc. was coated on the substrate and then heat treated at 120° C. for 5 hours to form a hole injection layer having a thickness of 50 nm. 70 wt % of CBP, 24 wt % of PVK, and 6 wt % of Complex 7 were mixed and then spin coated on the hole injection layer and heat treated at 110° C. for 2 hours to form an emission layer having a thickness of 60 nm. Then, a BAlq3 compound was vacuum deposited on the emission layer to a thickness of 30 nm to form a hole blocking layer. LiF and Al were sequentially vacuum deposited on the hole blocking layer to form an electron injection layer having a thickness of 0.8 nm and a cathode having a thickness of 150 nm. As a result, an organic light emitting device having a structure as illustrated in FIG. 1C was manufactured. The organic light emitting device prepared will now be referred to as Sample 7.

A plurality of organic light emitting devices were manufactured using Complexes 6, and 8 through 11 in the same manner as described above. These organic light emitting devices will be referred to as Samples 6, and 8 through 11, respectively.

An operating voltage, brightness, and efficiency of each of Samples 6 through 11 were measured using PR650 (Spectroscan) Source Measurement Unit.

TABLE 2

| Sample No. | Operating Voltage(V) | Maximum Current Efficiency (Cd/A) | Maximum external quantum efficiency(%) | Color Coordinate (10 mA/$cm^2$) |
| --- | --- | --- | --- | --- |
| 7 | 5 | 7.5 (at 19.5 V) | 10.4 | (0.68, 0.32) |
| 8 | 7 | 5.8 (at 21.5 V) | 9.8 | (0.64, 0.36) |
| 9 | 6 | 4.1 (at 16 V) | 8.5 | (0.63, 0.38) |
| 10 | 10 | 3.2 (at 21.5 V) | 6.5 | (0.67, 0.33) |
| 6 | 7 | 6.2 (at 20.5 V) | 9.2 | (0.66, 0.32) |
| 11 | 5 | 4.6 (at 16 V) | 9.3 | (0.67, 0.33) |

A cyclometalated transition metal complex according to the embodiments of the present invention contains a new ancillary ligand so that red light can be efficiently emitted using a phosphor through Intersystem crossing (ISC) of excitons into triplets and then metal to ligand charge transfer (MLCT). An organic light emitting device manufactured using the cyclometalated transition metal complex shows high luminous efficiency and external quantum efficiency.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A cyclometalated transition metal complex represented by one of Formulae 2 and 3:

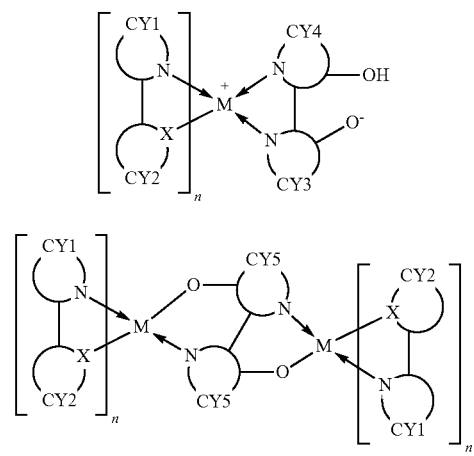

wherein M is Rh, Ir, Pt, or Au;

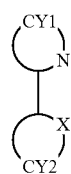

is a first mono anionic bidentate chelating ligand;

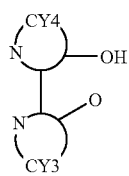

is a third mono anionic bidentate chelating ligand;

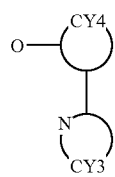

is a di-anionic tetradentate chelating ligand;

X is C, S, O, or N;

CY1, CY2, CY3, CY4 and CY5 are each independently an unsubstituted or substituted aromatic ring or an unsubstituted or substituted aliphatic ring; and n is 1 or 2.

2. The cyclometalated transition metal complex of claim 1, wherein the first mono anionic bidentate chelating ligand is selected from the group consisting of ligands represented by formulae below:

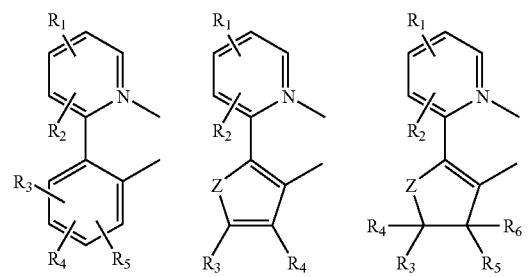

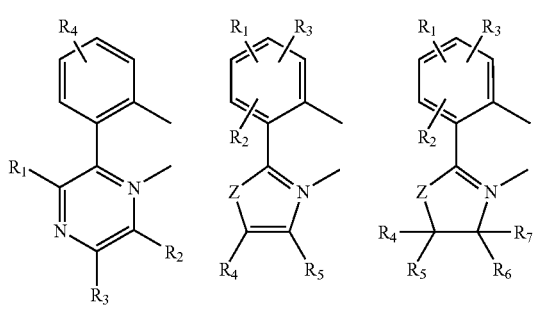

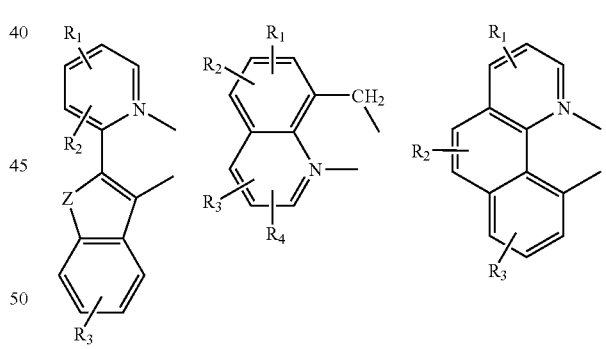

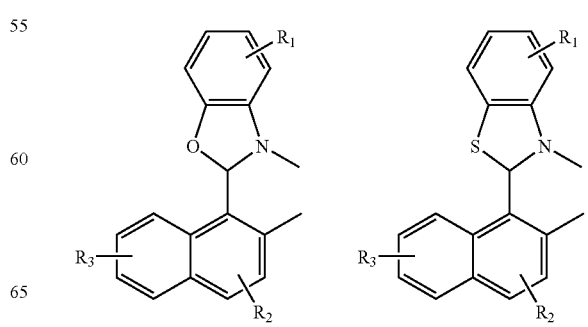

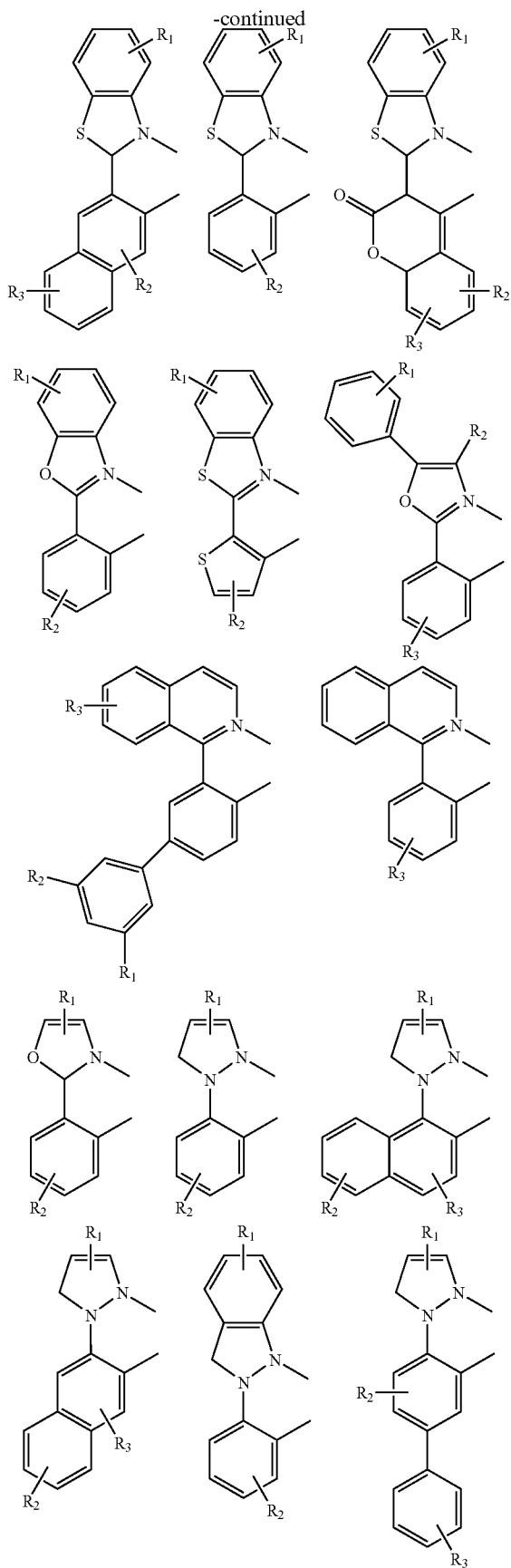

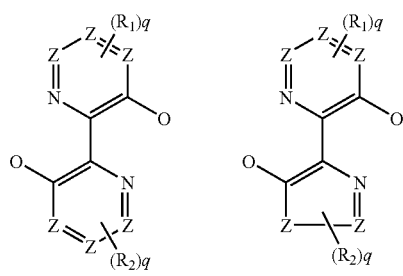

where Z is S, O, NR$_8$, and

R$_1$, R$_2$, R$_3$, R$_4$, R$_5$, R$_6$, R$_7$, and R$_8$ are each independently hydrogen, halogen, OH, CF$_3$, CN, silyl, alkyl, aryl, alkoxy, aryloxy, amino, or arylene, wherein adjacent Rs may be fused together to form a five to seven membered aliphatic or aromatic ring.

3. The cyclometalated transition metal complex of claim 1, wherein the third mono anionic bidentate chelating ligand is selected from the group consisting of ligands represented by formulae below:

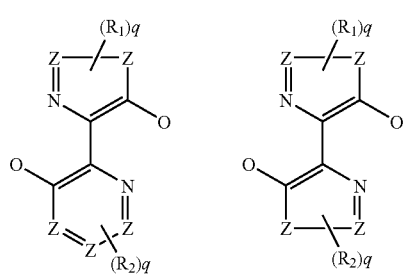

where Z is C;

q is an integer from 0 to 5; and

R$_1$ and R$_2$ are each independently hydrogen, halogen, OH, CF$_3$, CN, silyl, alkyl, aryl, alkoxy, aryloxy, amino, or arylene, wherein adjacent Rs may be fused together to form a five-to seven-membered aliphatic or aromatic ring.

4. The cyclometalated transition metal complex of claim 1, wherein the di-anionic tetradentate chelating ligand is selected from the group consisting of ligands represented by formulae below:

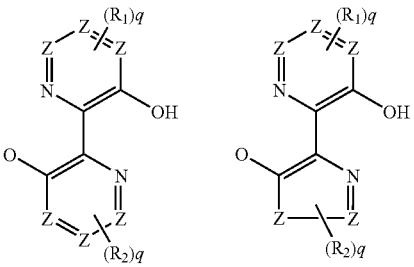

-continued

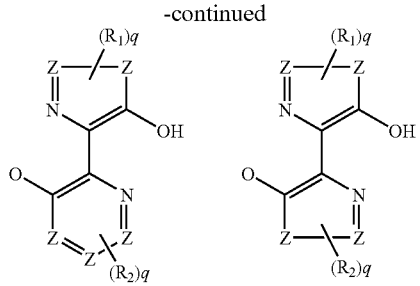

where Z is C;
q is an integer from 0 to 5; and
R$_1$ and R$_2$ are each independently hydrogen, halogen, OH, CF$_3$, CN, silyl, alkyl, aryl, alkoxy, aryloxy, amino, or arylene, wherein adjacent Rs may be fused together to form a five to seven membered aliphatic or aromatic ring.

5. The cyclometalated transition metal complex of claim 1, wherein the di-anionic tetradentate chelating ligand is selected from the group consisting of ligands represented by formulae below:

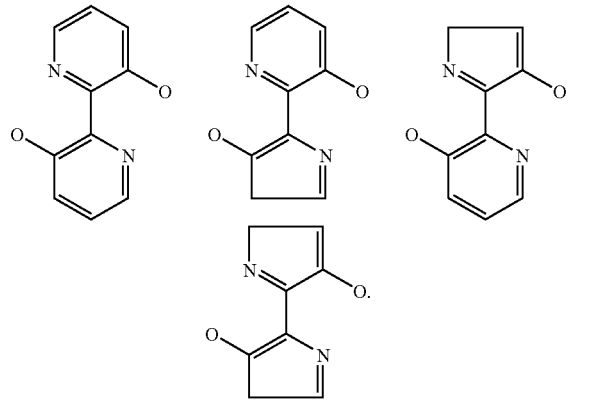

6. The cyclometalated transition metal complex of claim 1, wherein M is Ir.

7. The cyclometalated transition metal complex of claim 1 being a complex represented by one of the following Formulae 7 and 8:

(7)

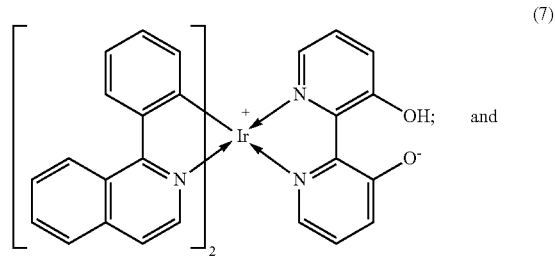

and (8)

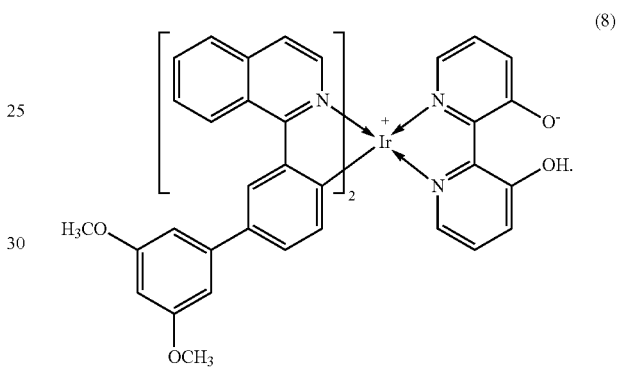

8. The cyclometalated transition metal complex of claim 1 being a complex represented by one of the following formulae 9 and 10 below:

(9)

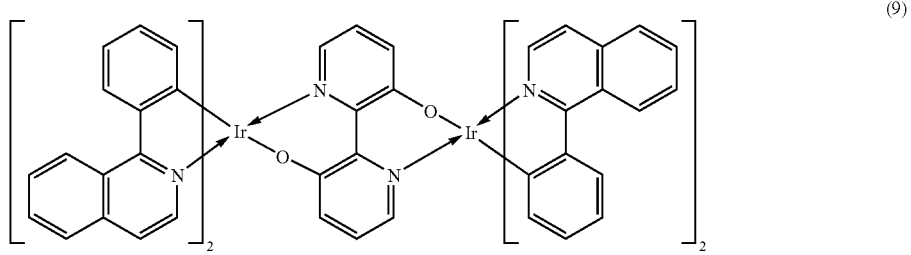

(10)

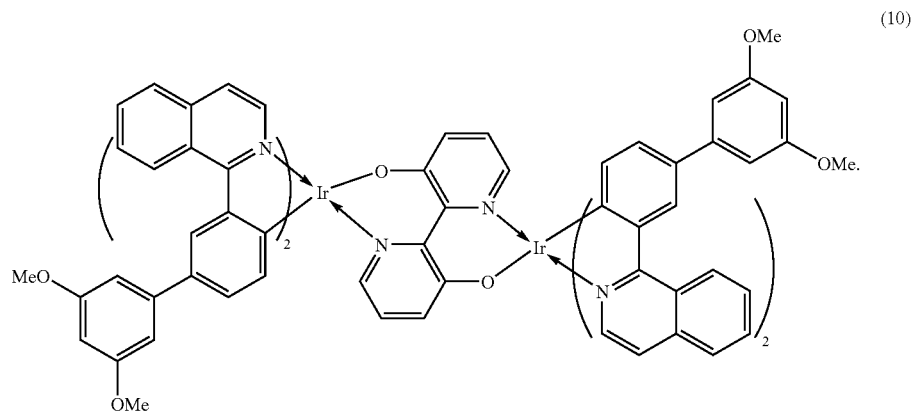

9. The cyclometalated transition metal complex of claim 1 being a complex represented by Formula 7:

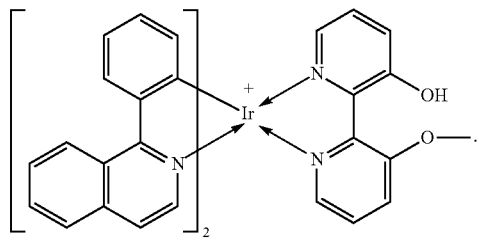

10. An organic light emitting device comprising an organic layer interposed between a pair of electrodes, the organic layer comprising the cyclometalated transition metal complex of claim 1.

11. The organic light emitting device of claim 10, wherein the organic layer further comprises at least one material selected from the group consisting of at least one kind of polymer host, a mixture of a polymer host and a low molecular weight host, a low molecular weight host, and a non-luminous polymer matrix.

12. The organic light emitting device of claim 10, wherein the organic layer further comprises a green light emitting material or a blue light emitting material.

13. A cyclometalated transition metal complex represented by one of Formulae 2 and 3:

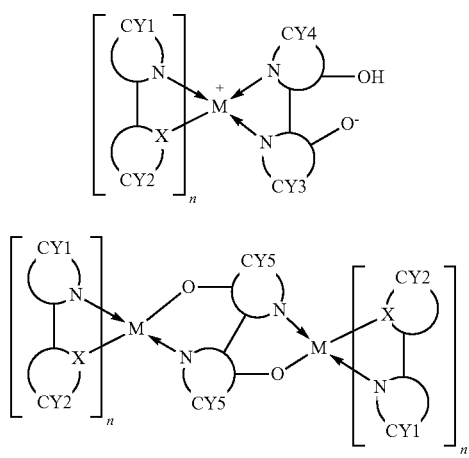

where M is a transition metal; and
n is 1 or 2;

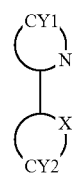

is a first mono anionic bidentate chelating ligand selected from the group consisting of ligands represented by formulae below:

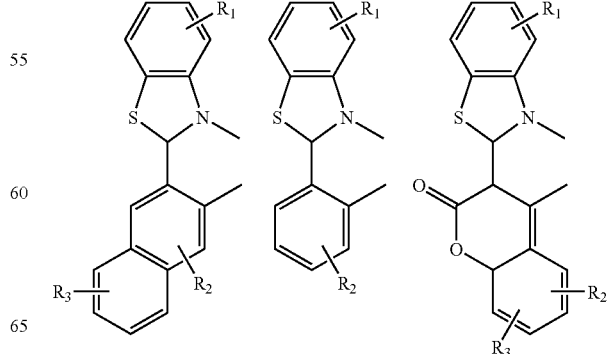

-continued

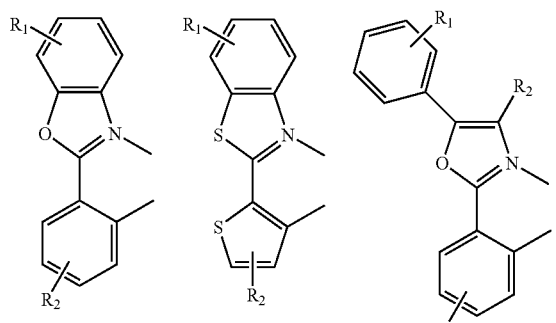

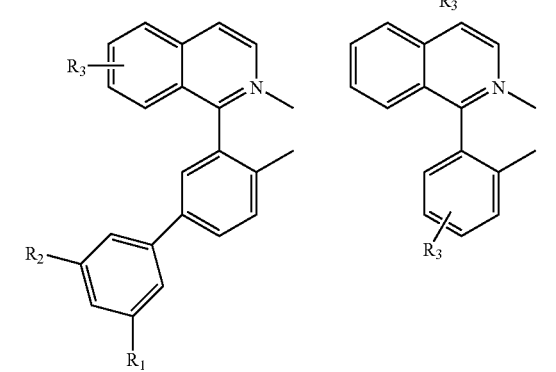

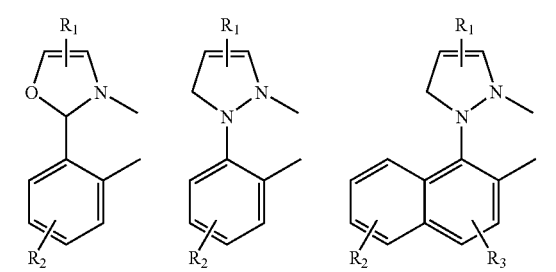

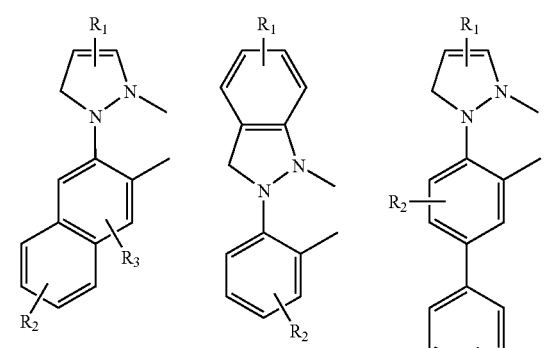

where Z is S, O, or NR$_8$, and

R$_1$, R$_2$, R$_3$, R$_4$, R$_5$, R$_6$, R$_7$, and R$_8$ are each independently hydrogen, halogen, OH, CF$_3$, CN, silyl, alkyl, aryl, alkoxy, aryloxy, amino, or arylene, wherein adjacent Rs may be fused together to form a five to seven membered aliphatic or aromatic ring;

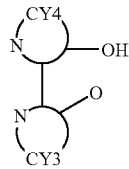

is a third mono anionic bidentate chelating ligand selected from the group consisting of ligands represented by formulae below:

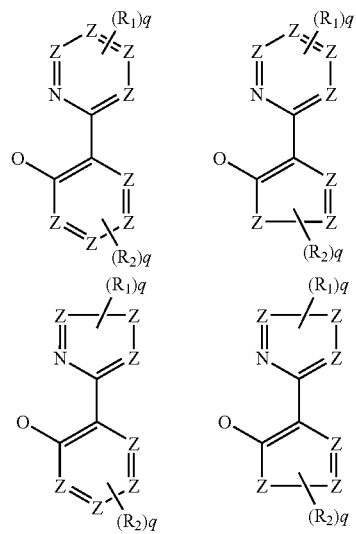

where Z is C;

q is an integer from 0 to 5; and

R$_1$ and R$_2$ are each independently hydrogen, halogen, OH, CF$_3$, CN, silyl, alkyl, aryl, alkoxy, aryloxy, amino, or arylene, wherein adjacent Rs may be fused together to form a five- to seven-membered aliphatic or aromatic ring; and

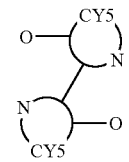

is a di-anionic tetradentate chelating ligand selected from the group consisting of ligands represented by formulae below:

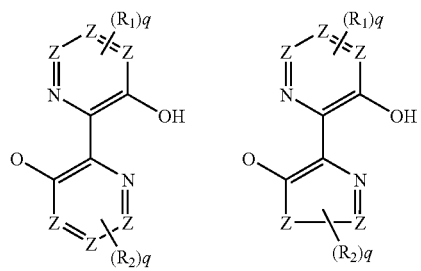

-continued

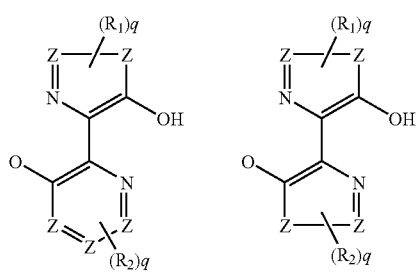

where Z is C;
q is an integer from 0 to 5; and
$R_1$ and $R_2$ are each independently hydrogen, halogen, OH, $CF_3$, CN, silyl, alkyl, aryl, alkoxy, aryloxy, amino, or arylene, wherein adjacent Rs may be fused together to form a five to seven membered aliphatic or aromatic ring.

14. An organic light emitting device comprising an organic layer interposed between a pair of electrodes, the organic layer comprising the cyclometalated transition metal complex of claim 13.

15. An organic light emitting device comprising:
a pair of electrodes; and
an emission layer interposed between the pair of electrodes, the organic layer comprising a cyclometalated transition metal complex represented by one of Formulae 2 and 3:

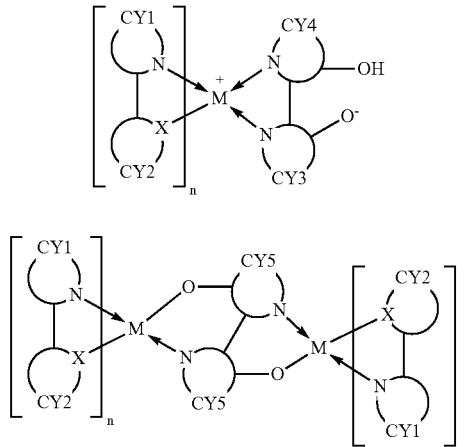

where M is a transition metal;

is a first mono anionic bidentate chelating ligand;

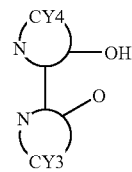

is a third mono anionic bidentate chelating ligand;

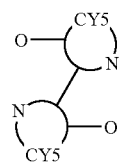

is a di-anionic tetradentate chelating ligand;
X is C, S, O, or N;
CY1, CY2, CY3, CY4 and CY5 are each independently an unsubstituted or substituted aromatic ring or an unsubstituted or substituted aliphatic ring; and
n is 1 or 2.

16. The organic light emitting device of claim 15, wherein the amount of the cyclometalated transition metal complex is in the range of 1 to 30 parts by weight based on 100 parts by weight of the total weight of the emission layer.

17. A cyclometalated transition metal complex represented by one of Formulae 2 and 3:

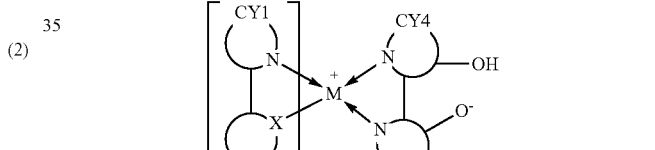

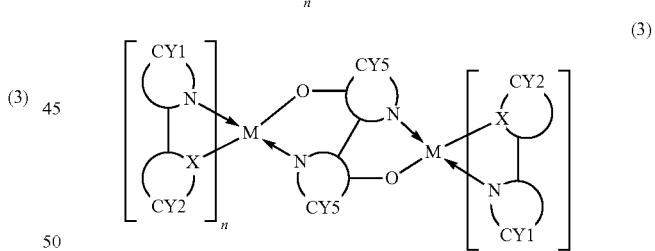

where M is a transition metal; and
n is 1 or 2;

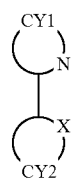

is a first mono anionic bidentate chelating ligand selected from the group consisting of ligands represented by formulae below:

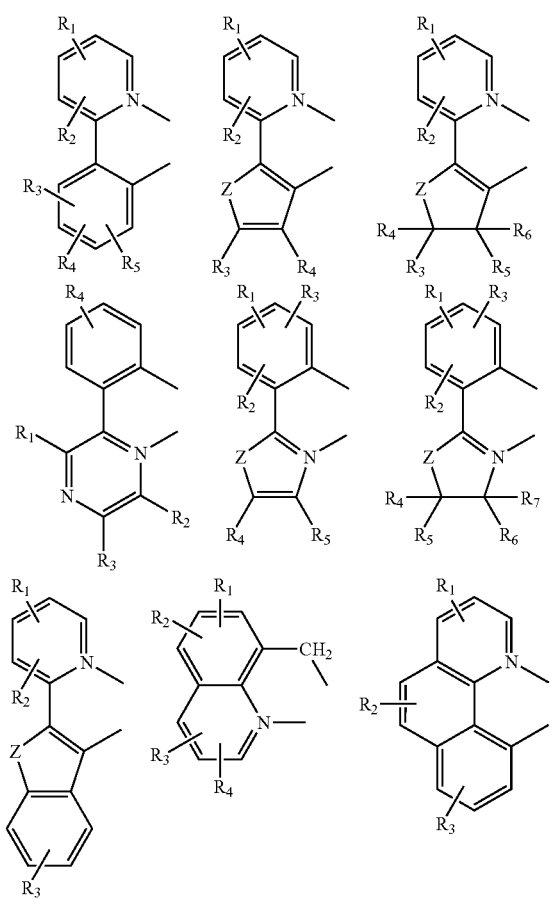
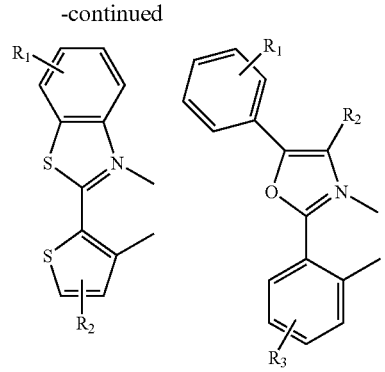
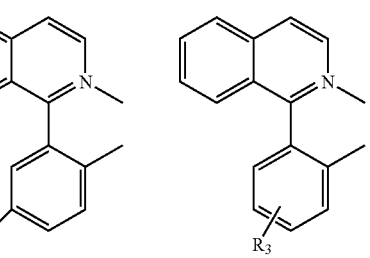
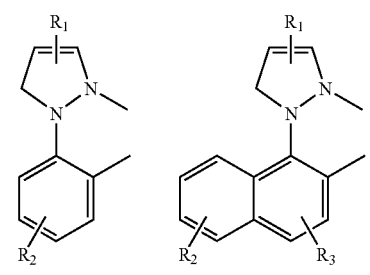
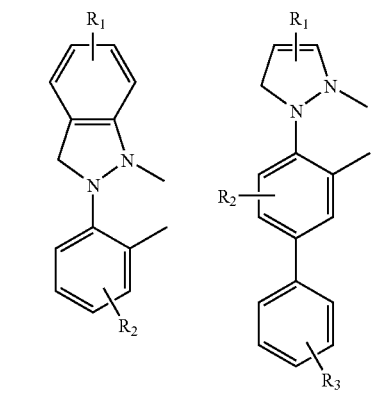

where Z is S, O, or $NR_8$, and $R_1$, $R_2$, $R_3$, $R_4$, $R_5$, $R_6$, $R_7$, and $R_8$ are each independently hydrogen, halogen, OH, $CF_3$, CN, silyl, alkyl, aryl, alkoxy, aryloxy, amino, or arylene, wherein adjacent Rs may be fused together to form a five to seven membered aliphatic or aromatic ring;

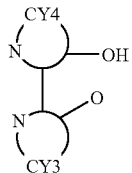

is a third mono anionic bidentate chelating ligand; and

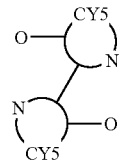

is a di-anionic tetradentate chelating ligand;

CY3, CY4 and CY5 are each independently an unsubstituted or substituted aromatic ring or an unsubstituted or substituted aliphatic ring; and n is 1 or 2.

* * * * *